United States Patent
Ryou et al.

(10) Patent No.: US 12,405,663 B2
(45) Date of Patent: Sep. 2, 2025

(54) SKIN-ATTACHABLE SENSOR SYSTEM AND METHOD FOR TRACKING EYE MOVEMENT AND POSITION

(71) Applicant: University of Houston System, Houston, TX (US)

(72) Inventors: Jae-Hyun Ryou, Houston, TX (US); Nam-In Kim, Houston, TX (US)

(73) Assignee: University of Houston System, Houston, TX (US)

( * ) Notice: Subject to any disclaimer, the term of this patent is extended or adjusted under 35 U.S.C. 154(b) by 0 days.

(21) Appl. No.: 18/571,815

(22) PCT Filed: Jun. 21, 2022

(86) PCT No.: PCT/US2022/034279
§ 371 (c)(1),
(2) Date: Dec. 19, 2023

(87) PCT Pub. No.: WO2022/271657
PCT Pub. Date: Dec. 29, 2022

(65) Prior Publication Data
US 2024/0281061 A1    Aug. 22, 2024

Related U.S. Application Data

(60) Provisional application No. 63/213,048, filed on Jun. 21, 2021.

(51) Int. Cl.
G06F 3/01    (2006.01)
(52) U.S. Cl.
CPC .................... *G06F 3/013* (2013.01)

(58) Field of Classification Search
None
See application file for complete search history.

(56) References Cited

U.S. PATENT DOCUMENTS

| | | | |
|---|---|---|---|
| 2006/0077064 A1 | 4/2006 | Baura | |
| 2015/0366504 A1* | 12/2015 | Connor | A61B 5/6804 600/301 |
| 2016/0270656 A1* | 9/2016 | Samec | A61B 3/1015 |
| 2017/0150897 A1 | 6/2017 | Komaki | |
| 2022/0350137 A1* | 11/2022 | Chung | G02B 27/0101 |

OTHER PUBLICATIONS

Kim et al., "Highly-sensitive skin-attachable eye-movement sensor using flexible nonhazardous piezoelectric thin film". Advanced Functional Materials. Feb. 2021; 31(8):2008242, abstract.
International Search Report and Written Opinion dated Nov. 17, 2022, for Application No. PCT/US2022/034279.

* cited by examiner

*Primary Examiner* — Stephen T. Reed
(74) *Attorney, Agent, or Firm* — Conley Rose, P.C.

(57) ABSTRACT

A system for tracking an eye of a user includes one or more piezoelectric sensors positionable on the face of the user, and an eye tracking computer system in signal communication with the one or more piezoelectric sensors so as to receive signals from the one or more piezoelectric sensors, wherein the computer system is configured to detect movement in at least one direction of the eye of the user based on the signals received by the computer system from the one or more piezoelectric sensors when the one or more piezoelectric sensors are positioned on the face of the user in one or more locations each spaced from the eyelids of the user.

15 Claims, 28 Drawing Sheets

SKIN-ATTACHABLE SENSOR SYSTEM AND METHOD FOR TRACKING EYE MOVEMENT AND POSITION

CROSS-REFERENCE TO RELATED APPLICATIONS

This application is a 35 U.S.C. § 371 national stage application of PCT/US2022/034279 filed Jun. 21 2022, entitled "Skin-Attachable Sensor System and Method for Tracking Eye Movement and Position", which claims benefit of U.S. provisional patent application Ser. No. 63/213,048 filed Jun. 21, 2021, and entitled "Skin-Attachable Sensor System and Method For Tracking Eye Movement and Position," which is hereby incorporated herein by reference in its entirety for all purposes.

STATEMENT REGARDING FEDERALLY SPONSORED RESEARCH OR DEVELOPMENT

Not applicable.

BACKGROUND

Tracking eye movement and position may be utilized in a variety of diverse applications including, for example, personal health and safety, public safety, medical diagnosis, and personal entertainment. With respect to personal health and safety, eye fatigue, which is commonly experienced when reading, writing, and driving for an extended period of time, has been identified as an important ocular health and safety problem. This problem is exasperated these days in view of the ever-increasing use of personal electronic devices. With respect to public safety, drowsiness and fatigue caused by, among other things, sleep deprivation, tiredness, circadian rhythm effect, and temporary brain circulation problems is a serious public safety hazard related to motor-vehicle and occupational accidents. Concerning medical diagnosis, the condition of a patient's eyes can reflect a corresponding condition of the patient's brain given that our eyes are one of the most connected organs to the brain through the body's central nervous system. Thus, the tracking of eye movement and position provides in at least some applications a simple yet efficient way to diagnose brain-related diseases in their early stages. Finally, concerning personal entertainment, eye-motion tracking has become an important component of virtual reality (VR) and augmented reality (AR) systems.

BRIEF SUMMARY OF THE DISCLOSURE

An embodiment of a system for tracking an eye of a user comprises one or more piezoelectric sensors positionable on the face of the user, and an eye tracking computer system in signal communication with the one or more piezoelectric sensors so as to receive signals from the one or more piezoelectric sensors, wherein the computer system is configured to detect movement in at least one direction of the eye of the user based on the signals received by the computer system from the one or more piezoelectric sensors when the one or more piezoelectric sensors are positioned on the face of the user in one or more locations each spaced from the eyelids of the user. In some embodiments, the computer system is configured to detect the movement in the at least one direction of the eye of the user when the one or more piezoelectric sensors are positioned on the temple of the user. In some embodiments, the one or more piezoelectric sensors comprises a plurality of the piezoelectric sensors positionable on the face of the user, and the computer system is configured to detect movement of the eye of the user in both a lateral direction and a vertical direction orthogonal to the lateral direction when the plurality of the piezoelectric sensors are positioned on the face of the user in a plurality of locations each spaced from the eyelids of the user. In certain embodiments, the computer system is configured to compare the signals produced by the plurality of the piezoelectric sensors to detect the movement of the eye of the user in both the lateral direction and the vertical direction when the plurality of the piezoelectric sensors are positioned on the face of the user in the plurality of locations each spaced from the eyelids of the user. In certain embodiments, the computer system is configured to detect movement of the eye of the user in a diagonal direction that is at a non-zero angle to both the lateral direction and the vertical direction when the plurality of the piezoelectric sensors are positioned on the face of the user in the plurality of locations each spaced from the eyelids of the user. In some embodiments, the computer system is configured to detect movement of the eye of the user in a rotational direction when the plurality of the piezoelectric sensors are positioned on the face of the user in the plurality of locations each spaced from the eyelids of the user. In some embodiments, the signals produced by the one or more piezoelectric sensors are contingent upon the deflection of the facial skin of the user upon which the one or more piezoelectric sensors are positioned. In certain embodiments, each of the one or more piezoelectric sensors comprises a pair of electrodes and a piezoelectric film positioned between the pair of electrodes. In certain embodiments, the piezoelectric film comprises at least one of aluminum nitride, gallium nitride, and indium nitride. In some embodiments, each of the one or more piezoelectric sensors comprises an outer insulating layer sealing the piezoelectric film and the pair of electrodes from the external environment. In some embodiments, each of the one or more piezoelectric sensors comprises an adhesive pad for removably attaching the one or more piezoelectric sensors to the face of the user. In certain embodiments, the computer system is configured to generate an image based on the detection of the movement of the eye of the user in the at least one direction, and the computer system comprises a visual display configured to indicate the image to the user.

An embodiment of a method for tracking an eye of a user comprises (a) producing signals from one or more piezoelectric sensors in response to the user moving their eye in at least one direction, wherein the one or more piezoelectric sensors are positioned on the face of the user in one or more locations each spaced from the eyelids of the user in response to the user, (b) receiving by a computer system the signals produced by the one or more piezoelectric sensors, and (c) detecting by the computer system movement in the at least one direction of the eye of the user based on the signals received from the one or more piezoelectric sensors. In some embodiments, (a) comprises producing signals from a plurality of the piezoelectric sensors in response to the user moving their eye in at least one direction, wherein the one or more piezoelectric sensors are positioned on the face of the user in one or more locations each spaced from the eyelids of the user in response to the user, (b) comprises receiving by the computer system the signals produced by the plurality of the piezoelectric sensors, and (c) comprises detecting by the computer system movement of the eye of the user in both a lateral direction and a vertical direction orthogonal to the lateral direction. In some embodiments, (c) comprises detecting by the computer system movement of the eye of the user in a diagonal direction that is at a non-zero angle to both the lateral direction and the vertical direction. In certain embodiments, (a) comprises producing signals from a plurality of the piezoelectric sensors in response to the user moving their eye in at least one direction, wherein the one or more piezoelectric sensors are positioned on the face of the user in one or more locations each spaced from the eyelids of the user in response to the user, (b) comprises receiving by the computer system the signals produced by the plurality of the piezoelectric sensors, and (c) comprises detecting by the computer system movement of the eye of the user in a rotational direction.

An embodiment of a computer system for tracking an eye of a user comprises a processor, and a storage device coupled to the processor and containing instructions that when executed cause the processor to detect movement in at least one direction of the eye of the user based on signals received by the computer system from one or more piezoelectric sensors when the one or more piezoelectric sensors are positioned on the face of the user in one or more locations each spaced from the eyelid of the user. In some embodiments, the instructions when executed cause the processor to detect movement of the eye of the user in both a lateral direction and a vertical direction orthogonal to the lateral direction when a plurality of the piezoelectric sensors are positioned on the face of the user in a plurality of locations each spaced from the eyelid of the user. In some embodiments, the instructions when executed cause the processor to detect movement of the eye of the user in a diagonal direction that is at a non-zero angle to both the lateral direction and the vertical direction when the plurality of the piezoelectric sensors are positioned on the face of the user in the plurality of locations each spaced from the eyelids of the user. In certain embodiments, the instructions when executed cause the processor to detect movement of the eye of the user in a rotational direction when a plurality of the piezoelectric sensors are positioned on the face of the user in a plurality of locations each spaced from the eyelids of the user.

An embodiment of a flexible piezoelectric sensor comprises a pair of electrically conductive electrodes, a piezoelectric film positioned between the pair of electrodes, the piezoelectric film comprising a Gallium Nitride material having a single-crystalline structure, and an electrical insulator sealing the pair of electrodes and the piezoelectric film from the surrounding environment, wherein the pair of electrodes are configured to produce an output voltage in response to a deflection of the piezoelectric film. In some embodiments, the Gallium Nitride material comprises a III-nitride material. In some embodiments, the piezoelectric film comprises at least one of Gallium Nitride (GaN), Aluminum Nitride (AlN), Scandium Nitride (ScN), and Indium Nitride (InN) in accordance with the formula of $In_xAl_ySc_zGa_{1-x-y}N$, where $0 \leq x \leq 1$, $0 \leq y \leq 1$, and $0 \leq z \leq 1$. In some embodiments, the thickness of the piezoelectric film is between 1.0 nanometer (nm) and 1.0 millimeter (mm). In certain embodiments, the piezoelectric sensor has a sensitivity between 0.5 volts per newton (V/N) and 5 V/N. In certain embodiments, the Gallium Nitride material has an outer sidewall having a surface roughness of 500 micrometers ($\mu$m) or less. In certain embodiments, the piezoelectric film is lead free. In some embodiments, the piezoelectric sensor comprises an adhesive pad coupled to the electrical insulator for releasably attaching the piezoelectric sensor to a surface.

An embodiment of a flexible piezoelectric sensor comprises a pair of electrically conductive electrodes, a piezoelectric film positioned between the pair of electrodes, the piezoelectric film comprising a Gallium material, and an electrical insulator sealing the pair of electrodes and the piezoelectric film from the surrounding environment, wherein the pair of electrodes are configured to produce an output voltage in response to a deflection of the piezoelectric film, wherein the piezoelectric sensor has a sensitivity between 0.1 volts per newton (V/N) and 5 V/N. In some embodiments, the sensitivity of the piezoelectric sensor is between 0.1 V/N and 1 V/N. In some embodiments, the Gallium Nitride material has an outer sidewall having a surface roughness of 500 micrometers ($\mu$m) or less. In certain embodiments, the surface roughness of the Gallium Nitride material is 100 $\mu$m or less. In certain embodiments, the Gallium Nitride material has a single-crystalline structure. In some embodiments, the piezoelectric film comprises at least one of Gallium Nitride (GaN), Aluminum Nitride (AlN), Scandium Nitride (ScN), and Indium Nitride (InN).

An embodiment of a method for forming a flexible piezoelectric sensor comprises (a) growing a piezoelectric film on a first substrate, wherein the piezoelectric film comprises a Gallium material and has an outer edge extending along the perimeter of the film, (b) trimming at least a portion of the outer edge from the piezoelectric film, and (c) coupling a pair of electrically conductive electrodes to the trimmed piezoelectric film whereby the trimmed piezoelectric film is positioned between the pair of electrodes. In some embodiments, the piezoelectric film comprises at least one of Gallium Nitride (GaN), Aluminum Nitride (AlN), Scandium Nitride (ScN) and Indium Nitride (InN). In some embodiments, the outer edge trimmed from the piezoelectric film is at least 0.5 millimeters (mm) in width. In certain embodiments, the method comprises (d) attaching a second substrate to one of the pair of electrodes, and (e) removing the first substrate from the piezoelectric film. In certain embodiments, the first substrate comprises Silicon and the second substrate comprises Sapphire. In some embodiments, the method comprises (d) enclosing the pair of electrodes and the trimmed piezoelectric film with an electrical insulator.

BRIEF DESCRIPTION OF THE DRAWINGS

For a detailed description of exemplary embodiments of the disclosure, reference will now be made to the accompanying drawings in which.

DETAILED DESCRIPTION

Figure 1:
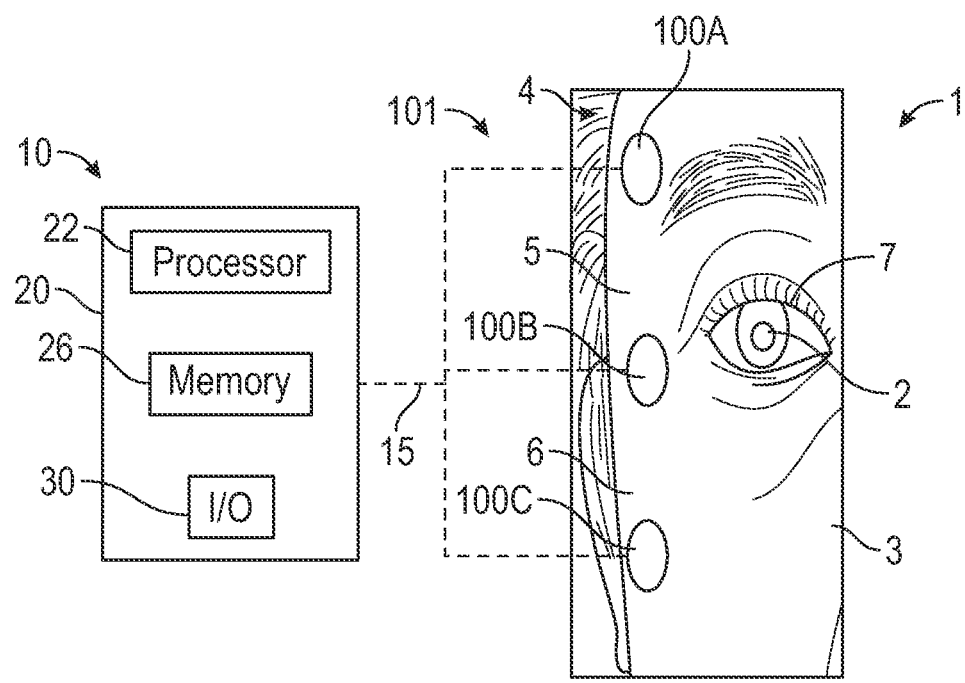
FIG. 1 is a schematic view of an embodiment of an eye tracking system.

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection, or through an indirect connection via other devices, components, and connections. In addition, as used herein, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis. As used herein, the terms "approximately," "about," "substantially," and the like mean within 10% (i.e., plus or minus 10%) of the recited value. Thus, for example, a recited angle of "about 80 degrees" refers to an angle ranging from 72 degrees to 88 degrees.

As described above, tracking of eye movement and position provides advantages in a wide variety of applications including, among others, personal health and safety, public safety, medical diagnosis, and personal entertainment. Conventional systems for tracking eye movement and position typically rely on computer vision-based approaches which can be broken down into remote eye tracking systems and head-mount-display (HMD)-embedded eye tracking systems. Remote eye tracking systems typically require expensive and bulky components such as a high-resolution camera, mounting units, and associated image processing software, generally preventing such systems from achieving miniaturization. Additionally, remote eye tracking systems require the localization of the user's head and eyes which may not be practical in applications in which the user's head moves relative to the camera of the remote eye tracking system. HMD-embedded eye tracking systems may address some of these challenges but introduce additional challenges in the form of cumbersome, uncomfortable, and expensive headgear worn by the user. Moreover, HMD-embedded eye tracking systems may not be employable in some applications in which the user cannot wear the eye tracking headgear such as when operating a motor vehicle.

Outside of computer vision-based approaches, another technique for tracking eye movement and position is electrooculography (EOG) in which a potential difference (the "EOG signal") between the cornea and retina of the user's eye is monitored and correlated with the position of the user's eye. However, the EOG signal relied upon for determining eye position is generally weak and thus easily influenced by external conditions. Thus, EOG based approaches are typically limited to applications under which the eye tracking is performed under controlled conditions such as with some medical diagnoses.

Accordingly, embodiments disclosed herein include systems and methods for tracking a user's eye using one or more piezoelectric sensors positionable on the user's face at one or more locations that are spaced from the user's eyelids and thus may be comfortably worn by the user. Additionally, embodiments of flexible piezoelectric sensors and methods for forming flexible piezoelectric sensors are described herein. The piezoelectric sensors may be formed from nontoxic (lead free) materials and thus may be safely worn by the user without posing risk to the user's health. The piezoelectric sensors have a sensitivity sufficiently great enough to detect the movement of the facial skin upon which the piezoelectric sensors are positions such that the sensors produce signals (e.g., one or more output voltages) that varies in response to movement of the facial skin. The piezoelectric sensor may comprise a Gallium Nitride material having a single-crystalline structure providing the piezoelectric sensor with both sufficient flexibility and sensitivity. As will be described further herein, the Gallium Nitride material may comprise a III-Nitride material including Aluminum Nitride and Aluminum Gallium Nitride. Additionally, a piezoelectric thin film of the sensor comprising the Gallium Nitride material may be trimmed during the process of forming the sensor to free the thin film from microcracks or other flaws which tend to occur along the outer edge of the thin film, thereby maximizing the durability of the piezoelectric sensor.

Embodiments of eye tracking systems disclosed herein include an eye tracking computer system which receives signals from the one or more piezoelectric sensors and detects movement of the user's eye in one or more directions based on the received signals. As will be described further herein, eye tracking systems disclosed herein may include a plurality of piezoelectric sensors positioned at different locations on the user's face (each spaced from the eyelids of the user) to permit the system to detect movement both laterally, vertically, diagonally, and rotationally. This information (e.g., current direction and/or rate of travel of the eye, current position of the eye, etc.) may be utilized in generating one or more images by the eye tracking system which may then be indicated to the user by the eye tracking computer system. For example, the position and/or movement of the user's eye may be utilized in generating a VR or AR environment.

Referring now to FIG. 1, an embodiment of an eye tracking system 10 for tacking the movement and position of an eye 2 of a user 1 is shown. In this exemplary embodiment, eye tracking system 10 generally includes an eye tracking computer system 20 and a plurality of flexible, skin-attachable, flexible piezoelectric sensors 100A-100C which form a sensor network 101 of the eye tracking system 10. As will be described further herein, computer system 20 tracks the movement and position of the user's eye 2 based on signals provided to the computer system 20 from the plurality of piezoelectric sensors 100A-100C. Computer system 20 is thus in signal communication with the plurality of piezoelectric sensors 100A-100C via a signal connection or pathway 15 formed therebetween. The signal connection 15 may be wired with computer system 20 located proximal the plurality of piezoelectric sensors 100A-100C. Alternatively, signal connection 15 may be wireless with computer system 20 located proximal or distal (or both with a portion of system 20 proximal and a portion of system 20 distal) the plurality of piezoelectric sensors 100A-100C. For example, the plurality of piezoelectric sensors 100A-100C may each include a wireless transmitter for communicating wirelessly with the computer system 20.

In this exemplary embodiment, computer system 20 generally includes a processor 22 (which may be referred to as a central processor unit or CPU) that is in communication with one or more memory devices 26, and input/output (I/O) devices 30. The processor 22 may be implemented as one or more CPU chips. The memory devices 26 of computer system 20 may include secondary storage (e.g., one or more disk drives, etc.), a non-volatile memory device such as read only memory (ROM), and a volatile memory device such as random-access memory (RAM). In some contexts, the secondary storage ROM, and/or RAM comprising the memory devices 26 of computer system 20 may be referred to as a non-transitory computer readable medium or a computer readable storage media. I/O devices 30 may include printers, video monitors, liquid crystal displays (LCDs), touch screens, keyboards, keypads, switches, dials, mice, and/or other well-known input devices. Although shown as including a single CPU 22, and a single memory device 26, it may be understood that computer system 20 may include a plurality of separate CPUs 22, memory devices 26, and I/O devices 30. It may also be understood that computer system 20 may be embodied in a networked computing system such as a cloud computing environment in which, for example, components of computer system 20 are executed and/or stored in the cloud rather than locally on a single computer.

It is understood that by programming and/or loading executable instructions onto the computer system 20, at least one of the CPU 22, the memory devices 26 are changed, transforming the computer system 20 in part into a particular machine or apparatus having the novel functionality taught by the present disclosure. Additionally, after the computer system 20 is turned on or booted, the CPU 22 may execute a computer program or application. For example, the CPU 22 may execute software or firmware stored in the memory devices 26. During execution, an application may load instructions into the CPU 22, for example load some of the instructions of the application into a cache of the CPU 22. In some contexts, an application that is executed may be said to configure the CPU 22 to do something, e.g., to configure the CPU 22 to perform the function or functions promoted by the subject application. When the CPU 22 is configured in this way by the application, the CPU 22 becomes a specific purpose computer or a specific purpose machine.

Piezoelectric sensors 100A-100C of eye tracking system 10 are positionable on a face 3 of the user 1 to monitor physiological phenomena of the user 1. In this exemplary embodiment, piezoelectric sensors 100A-100C comprise piezoelectric sensors which, when positioned on the user's face 3, produce electrical signals in response to flexing or other movement of the user's facial skin in response to the user 1 moving their eye 2. Piezoelectric sensors 100A-100C may thus also be referred to herein as piezoelectric sensors 100A-100C. As will be discussed further herein, piezoelectric sensors 100A-100C each comprise a piezoelectric film including Gallium Nitride, Aluminum Gallium Nitride, and Aluminum Nitride. The piezoelectric sensors 100A-100C may be removably or releasably attached in a comfortable and safe manner to the user's face 3 through a variety of means including, for example, adhesive pads, suction cups, or other releasable connectors.

It may be understood that movement of the eye 2 is controlled by a network of several distinct muscles known as the extraocular muscles. The action of the extraocular muscles produces, along with movement of the user's eye 2, movement in the user's skin positioned around the extraocular muscles. This movement of the user's skin may result in the mechanical deflection of a piezoelectric sensor 100 (e.g., one of piezoelectric sensors 100A-100C shown in FIG. 1) positioned on the moving skin, thereby causing the piezoelectric sensor 100 to produce or modulate an electrical signal. The degree of mechanical deflection produced in a given piezoelectric sensor 100 is contingent upon the direction of movement of the user's eye 2 (dependent upon which of the extraocular muscles are activated) and the position of the given piezoelectric sensor 100 on the user's face 3. In this exemplary embodiment, a first or upper piezoelectric sensor 100A is positioned on an upper temple area 4, a second or middle piezoelectric sensor 100B is positioned on a middle temple area 5, and a third or lower piezoelectric sensor 100C is positioned on a lower temple area 6 of the user's face 3. However, it may be understood that piezoelectric sensors 100A-100C may be positioned at various locations on the user's face 3 such as user's forehead, the user's cheek and other locations upon which a given piezoelectric sensor 100 of eye tracking system 10 may be safely and comfortably worn by the user 1. In other words, sensitive parts of the user's face 3 such as the user's eyelid 7 may be avoided when positioning piezoelectric sensors 100A-100C on the user's face 3.

Figure 2:
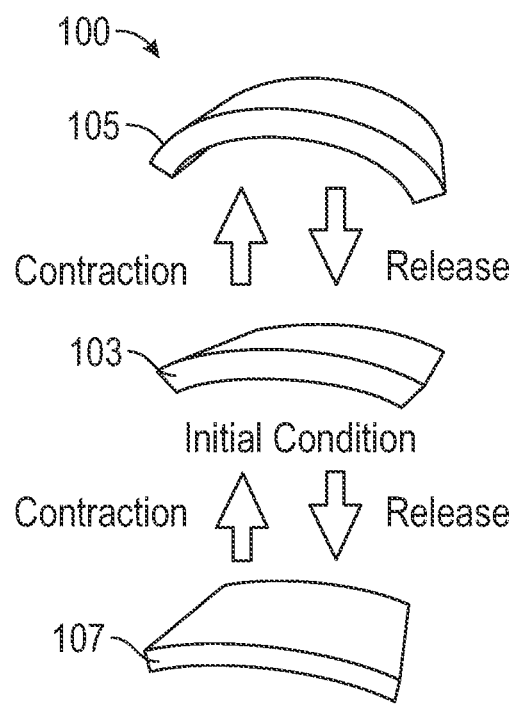
FIG. 2 is a perspective view of an embodiment of a piezoelectric sensor of the eye tracking system of FIG. 1.
Figure 3:
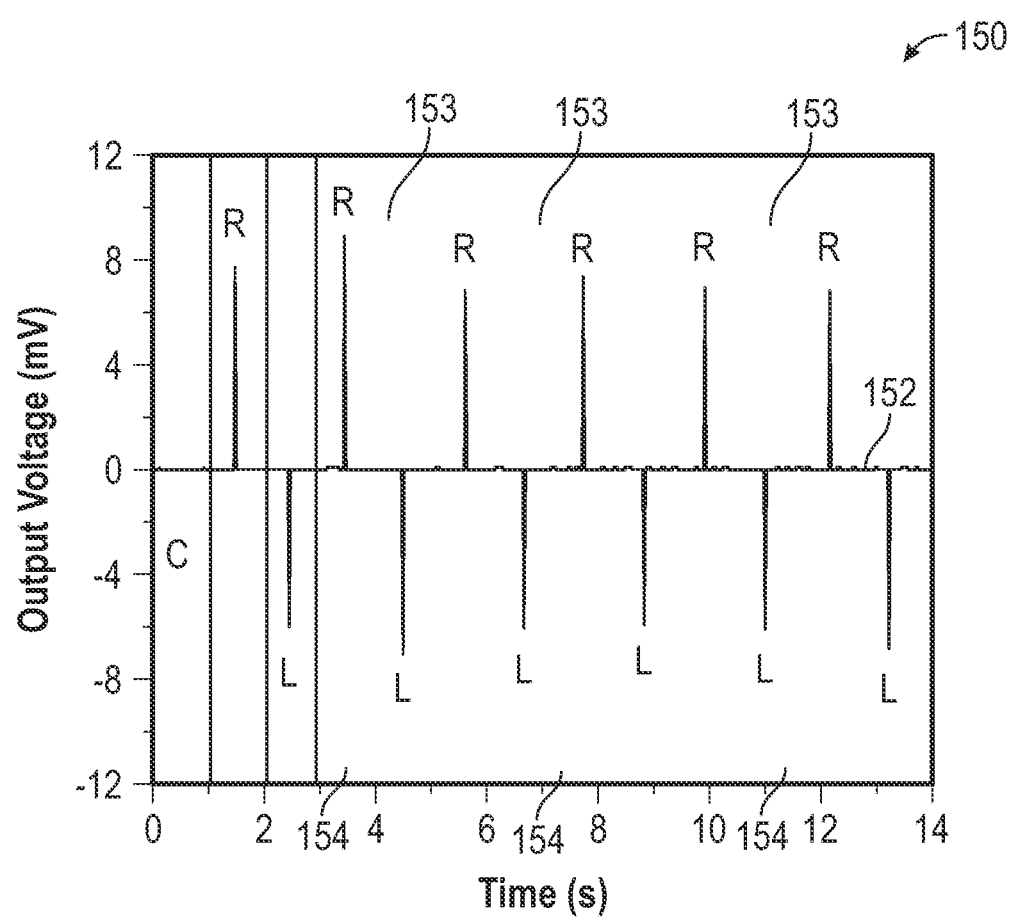
FIG. 3 is a graph illustrating an output voltage of a piezoelectric sensor as a function of time.

Referring to FIGS. 1-3, aspects of the operation of eye tracking system 10 are illustrated schematically in FIGS. 2 and 3. Particularly, FIG. 2 illustrates schematically one of the piezoelectric sensors 100 of eye tracking system 10 in an initial state 103, a first flexed state 105, and a third flexed state 107. The initial state 103 of piezoelectric sensor 100 corresponds to the state or shape of piezoelectric sensor 100 when piezoelectric sensor is positioned on the temple area (e.g., one of temple areas 4, 5, and 6 of user 1) of a user with the user looking centrally or straight ahead. The first flexed state 105 of piezoelectric sensor 100 corresponds to the user moving their eye laterally in the direction of the temple area (with the piezoelectric sensor 100 placed on the temple area), while the second flexed state 107 corresponds to the user moving their eye laterally in the opposing direction away from the temple area. As can be seen in FIG. 2, piezoelectric sensor 100 is deflected or contracted as it transitions from the initial state 103 to the first flexed state 105 such that a degree of curvature along the piezoelectric sensor 100 increases as the piezoelectric sensor 100 moves from the initial state 103 to the first flexed state 105. Conversely, piezoelectric sensor 100 is deflected as it transitions from the initial state 103 to the second flexed state 107 whereby the degree of curvature along the sensor 100 decreases as the sensor 100 moves from the initial state 103 to the second flexed state 107.

The change in deflection along piezoelectric sensor 100 alters an electrical voltage produced by the sensor 100. Particularly, a change in deflection along sensor 100 may change both a magnitude and a polarity of the electrical voltage produced by piezoelectric sensor 100. FIG. 3 illustrates a graph 150 of electrical voltage signal or output 152 produced by the sensor 100 as a user, beginning in an initial pose looking centrally straight ahead, alternatingly looks laterally to the right (towards the piezoelectric sensor 100 positioned on the user's temple) and left (away from the piezoelectric sensor 100). As shown by graph 150, the user moving his eye towards the right (transitioning piezoelectric sensor 100 into the first flexed state 105) produces a series of positive polarity peaks 153 of the voltage output 152. Conversely, the user moving his eye towards the left (transitioning sensor 100 into the second flexed state 107) produces a series of negative polarity peaks 154 (having an opposed plurality to the positive polarity peaks 153) of the voltage output 152. However, the voltage output 152 of piezoelectric sensor 100 is substantially zero when sensor 100 is in the initial state 103. Thus, further bending of piezoelectric sensor 100 from the initial state 103 (e.g., into the first flexed state 105) results in sensor 100 producing a positive electrical voltage, while the straightening out of sensor 100 from the initial state 103 (e.g., into the second flexed state 107) produces a negative electrical voltage from the sensor 100. Graph 150 thus illustrates how the magnitude and polarity of the voltage produced the piezoelectric sensor 100. By correlating the magnitude and polarity of the voltage output of the piezoelectric sensor 100 with the current position of the user's eye, the position of the user's eye may be monitored or tracked via the electrical voltage produced by sensor 100.

While FIGS. 2 and 3 illustrate that a single piezoelectric sensor 100 may be used to track the position of a user's eye in the lateral direction (moving between left and right), the eye tracking system 10 is configured to track the position of the user's eye 2 in both the lateral and vertical directions, as well as combinations thereof (e.g., in a diagonal direction by looking towards the "corner" of the eye, in a rotational direction by "rolling" the eye, etc.). This is accomplished by integrating the signals produced by two or more separate piezoelectric sensors (e.g., piezoelectric sensors 100A-100C) attached to the user's face at different locations to form a sensor network.

Figure 4:
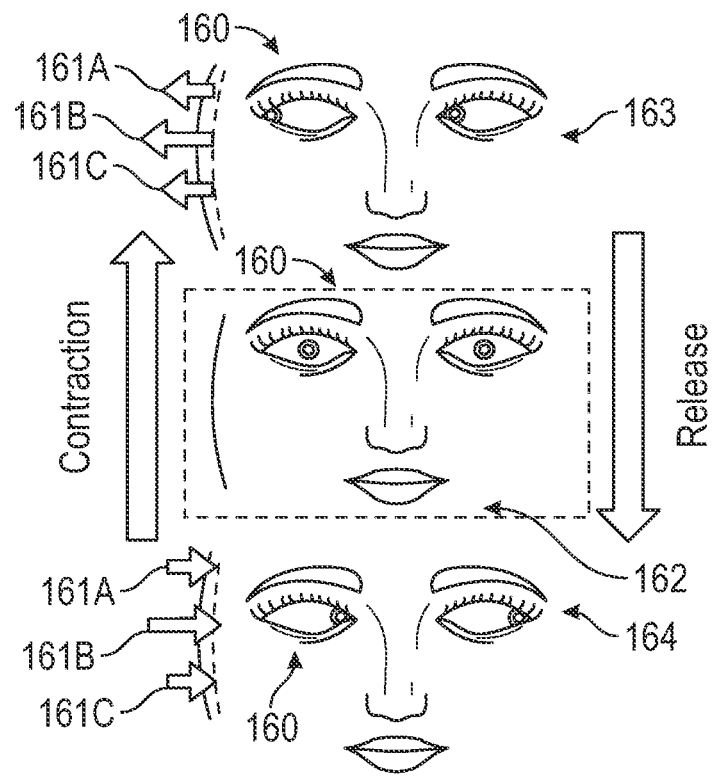
FIGS. 4 and 5 are schematic views of an output voltage response of a plurality of piezoelectric sensors responding to movement of a user's eye.
Figure 5:
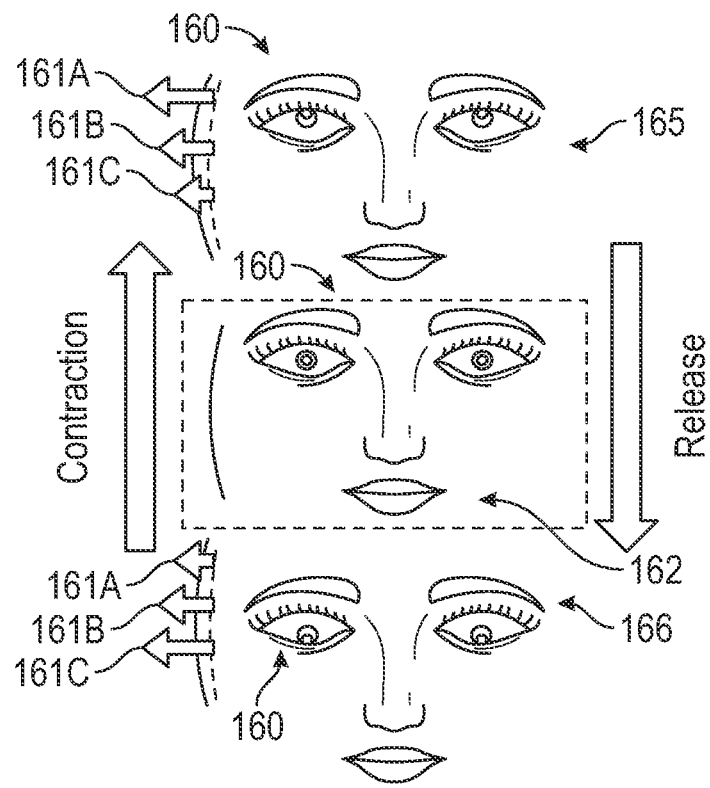
Figure 6:
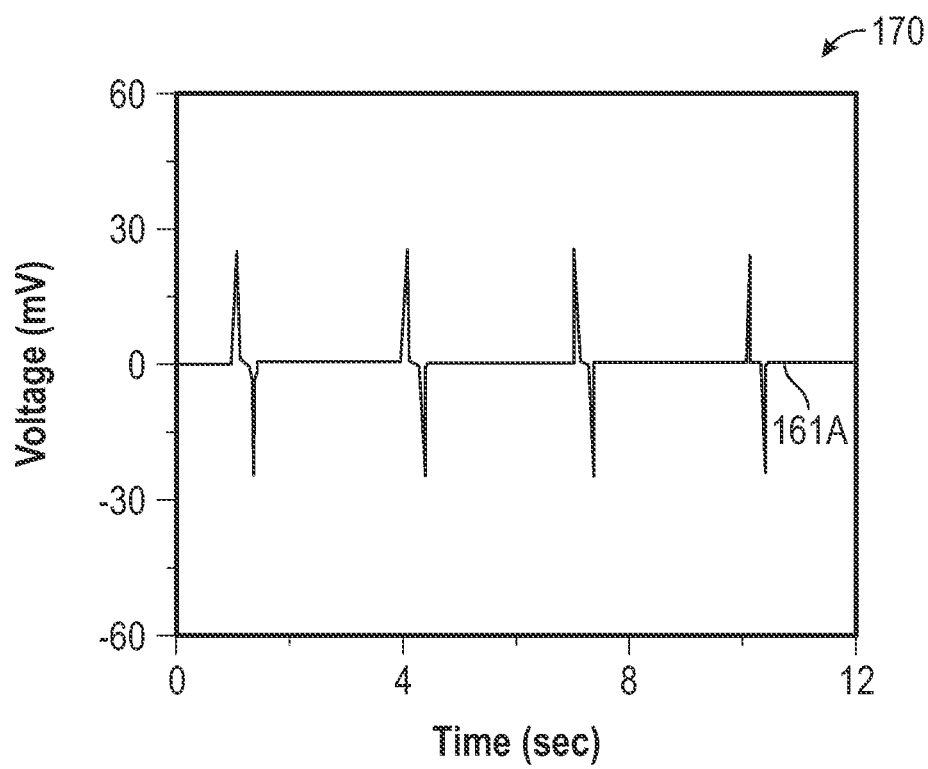
FIG. 6 is a graph illustrating an output voltage of a first piezoelectric sensor of the plurality of piezoelectric sensors of FIG. 4 as a function of time.
Figure 7:
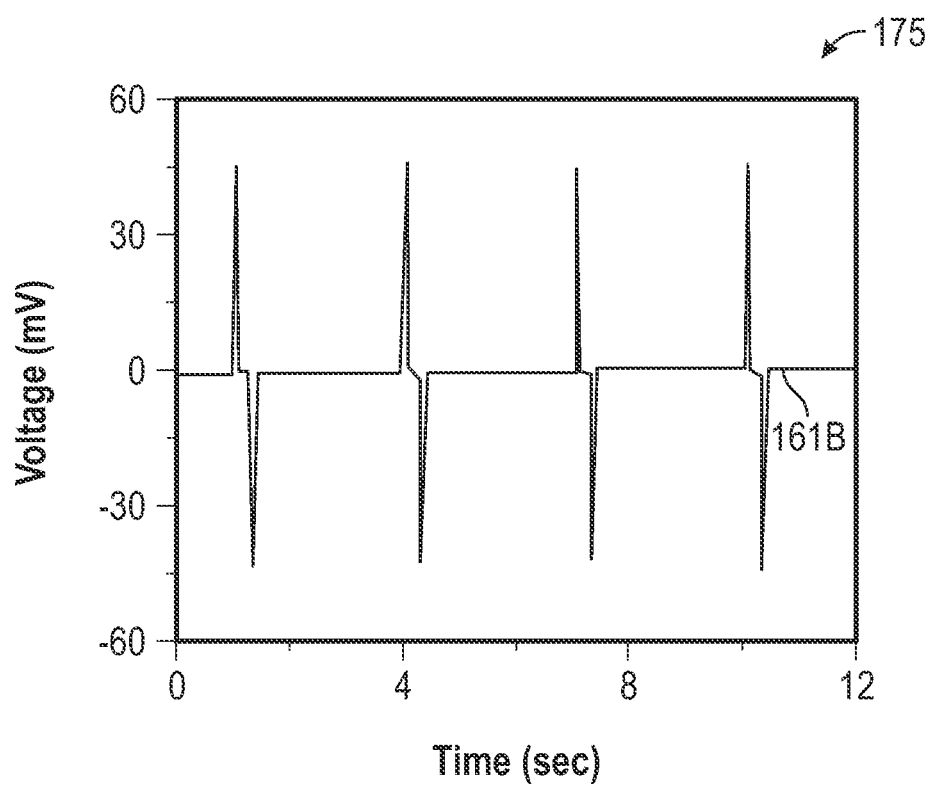
FIG. 7 is a graph illustrating an output voltage of a second piezoelectric sensor of the plurality of piezoelectric sensors of FIG. 4 as a function of time.
Figure 8:
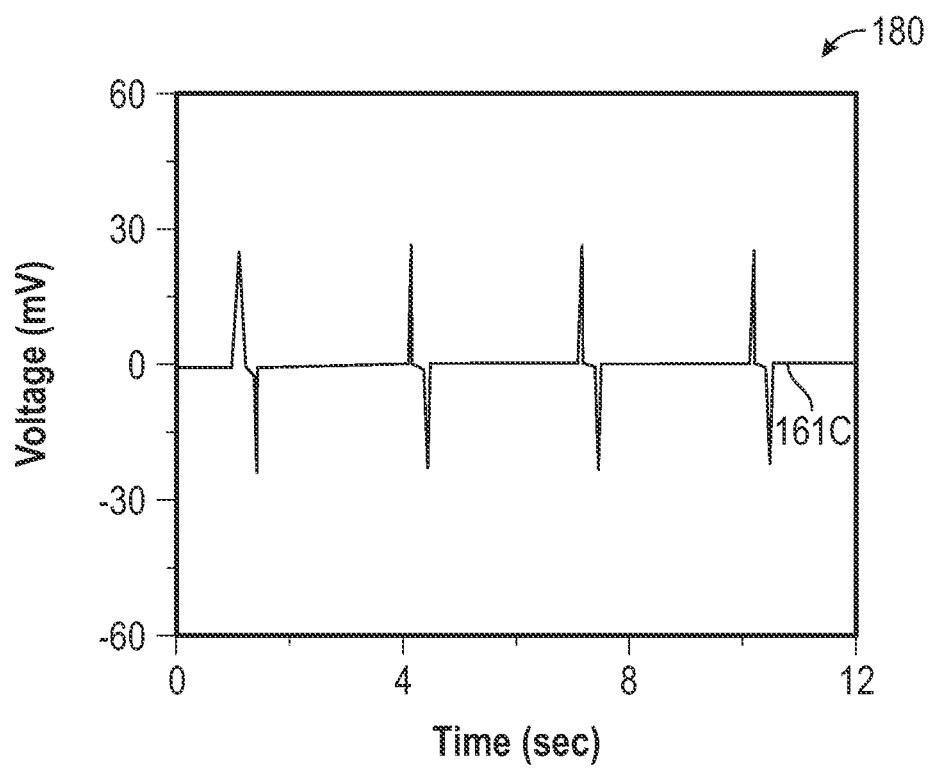
FIG. 8 is a graph illustrating an output voltage of a third piezoelectric sensor of the plurality of piezoelectric sensors of FIG. 4 as a function of time.
Figure 9:
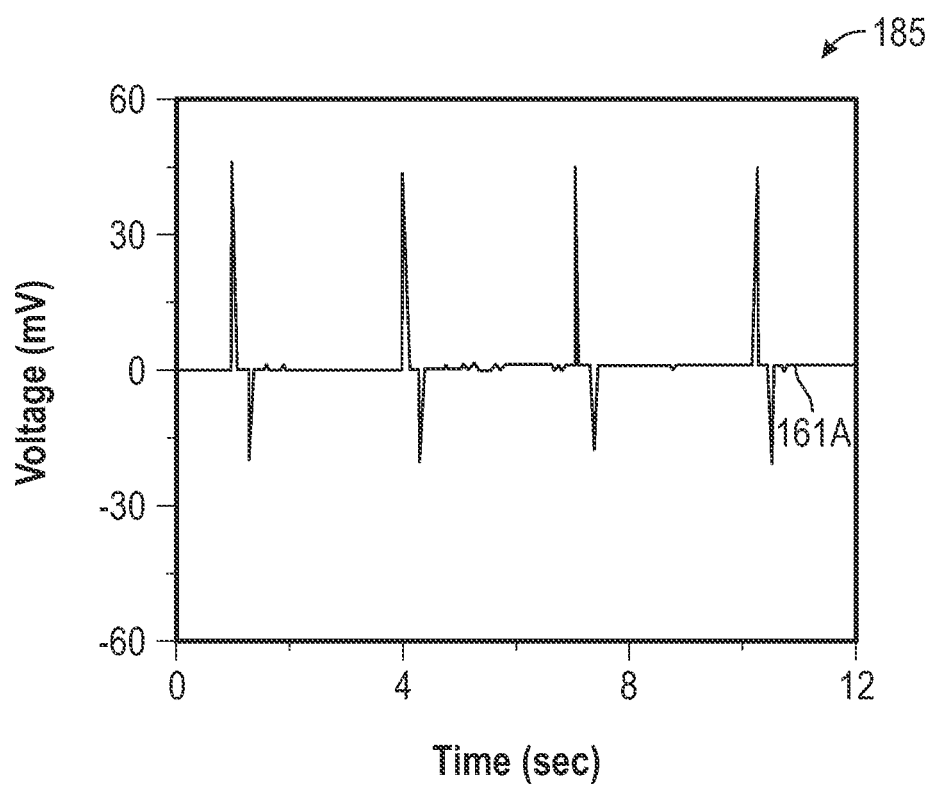
FIG. 9 is a graph illustrating an output voltage of a first piezoelectric sensor of the plurality of piezoelectric sensors of FIG. 5 as a function of time.
Figure 10:
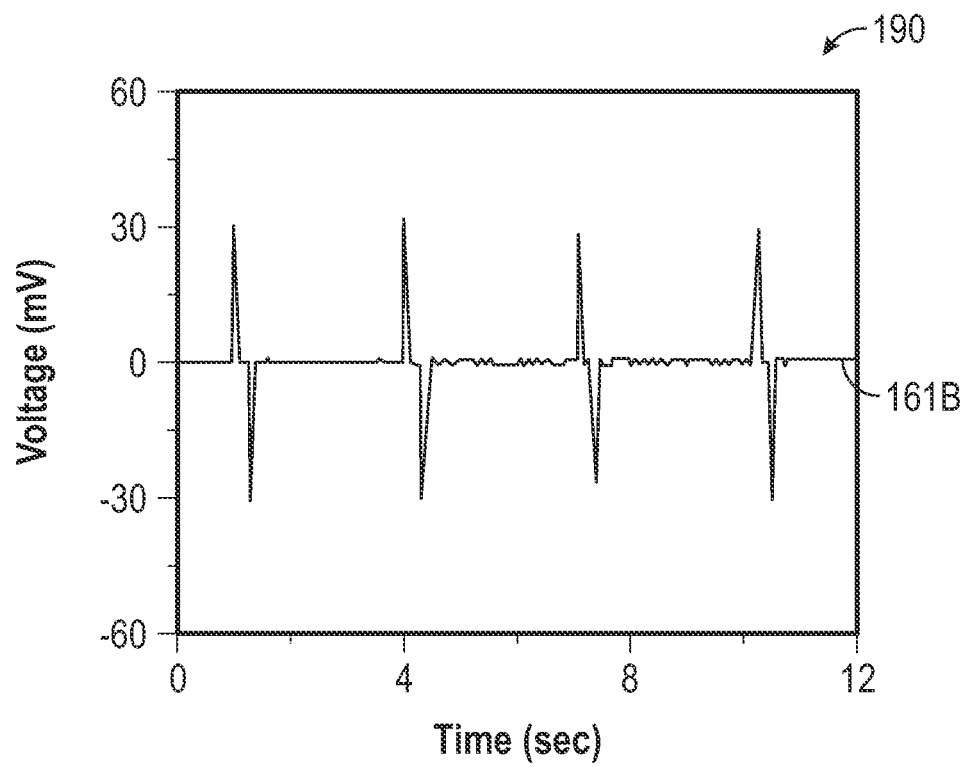
FIG. 10 is a graph illustrating an output voltage of a second piezoelectric sensor of the plurality of piezoelectric sensors of FIG. 5 as a function of time.
Figure 11:
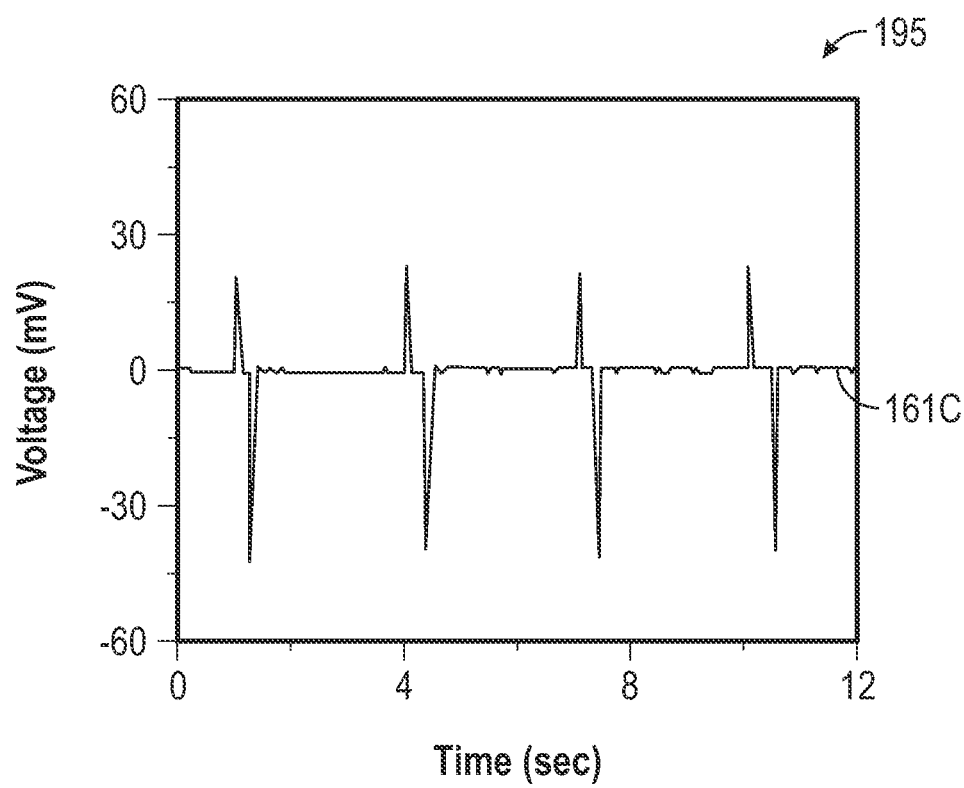
FIG. 11 is a graph illustrating an output voltage of a third piezoelectric sensor of the plurality of piezoelectric sensors of FIG. 5 as a function of time.

Referring now to FIGS. 1 and 4-11, additional aspects of the operation of eye tracking system 10 are illustrated schematically in FIGS. 4-11. Particularly, FIGS. 4 and 5 illustrate exemplary electrical voltage signals or outputs 161A-161C for piezoelectric sensors 100A (positioned on upper temple area 4), 100B (positioned on middle temple area 5), and 100C (positioned on lower temple area 6), respectively, in response to a user 160 looking centrally straight ahead (indicated by arrow 162 in FIGS. 4 and 5), laterally to the left (indicated by arrow 163 in FIG. 4), laterally to the right (indicated by arrow 164 in FIG. 4), vertically upwards (indicated by arrow 165 in FIG. 5), and vertically downwards (indicated by arrow 166 in FIG. 5).

In this example, when the user's eye moves, the deflection of skin behaves similarly as described earlier with respect to FIGS. 3 and 4; however, the degree of deflection in different sensing locations (the locations at which the sensors 100A-100C are attached) are different, resulting in the different magnitude of voltage signals 161A-161C from each piezoelectric sensor 100A-100C, respectively. In the case of lateral eye movement shown in FIG. 4, the muscles around the user's eye, such as the lateral rectus and medial rectus, are mainly used. The muscles and ligaments underneath the temple area of the user 160 are contracted and expanded depending on the direction of the lateral eye movements. For pure lateral movement shown in FIG. 4, the magnitude of the voltage output 161B of middle piezoelectric sensor 100B is greater than the voltage outputs 161A and 161C of piezoelectric sensors 100A and 100C, respectively, which are similar to each other. Graphs 170, 175, and 180 shown in FIGS. 6-8, respectively, illustrate voltage output 161A (graph 170), voltage output 161B (graph 175), and voltage output 161C (graph 180) as the user 160 looks alternatingly in the lateral left and right directions as indicated in FIG. 4. As shown by graphs 170, 175, and 180, the magnitude of both the positive and negative polarity peaks of the voltage output 176 of middle piezoelectric sensor 100B is greater than the positive and negative polarity peaks of voltage outputs 171 and 181. It may be observed from these examples that the piezoelectric sensor 100 most greatly aligned with the direction of movement of the eye or in closest proximity to the position of the eye (middle piezoelectric sensor 100B in the example of FIGS. 4 and 6-8) has the great voltage output.

For a pure vertically upward movement shown in FIG. 5, the magnitude of the voltage output 161A of upper piezoelectric sensor 100A is greater than the voltage outputs 161B and 161C of piezoelectric sensors 100B and 100C, respectively, while the voltage output 161B of piezoelectric sensor 100B is greater than voltage output 161C of piezoelectric sensor 100C. Conversely, for a pure vertically downward movement also shown in FIG. 5, the magnitude of the voltage output 161C of lower piezoelectric sensor 100C is greater than the voltage outputs 161B and 161A of piezoelectric sensors 100B and 100A, respectively, while the voltage output 161B of piezoelectric sensor 100B is greater than voltage output 161A of piezoelectric sensor 100A. Graphs 185, 190, and 195 shown in FIGS. 9-11, respectively, illustrate voltage output 161A (graph 185), voltage output 161B (graph 190), and voltage output 161C (graph 195) as the user 160 looks alternatingly in the vertically upwards and downwards directions as indicated in FIG. 5. As shown by graph 185, the magnitude of the positive polarity peaks (corresponding to the user 160 looking vertically upwards) of voltage output 161A is greater than the magnitude of the negative polarity peaks 187 of voltage output 161A (corresponding to the user 160 looking vertically downwards). Conversely, and as shown by graph 195, the magnitude of the positive polarity peaks (corresponding to the user 160 looking vertically upwards) of voltage output 161C is less than the magnitude of the positive polarity peaks of voltage output 161C (corresponding to the user 160 looking vertically downwards). Finally, as shown by graph 190, the magnitude of the positive polarity peaks of voltage output 161B is substantially equal to the magnitude of the negative polarity peaks of voltage output 161B.

Figure 12:
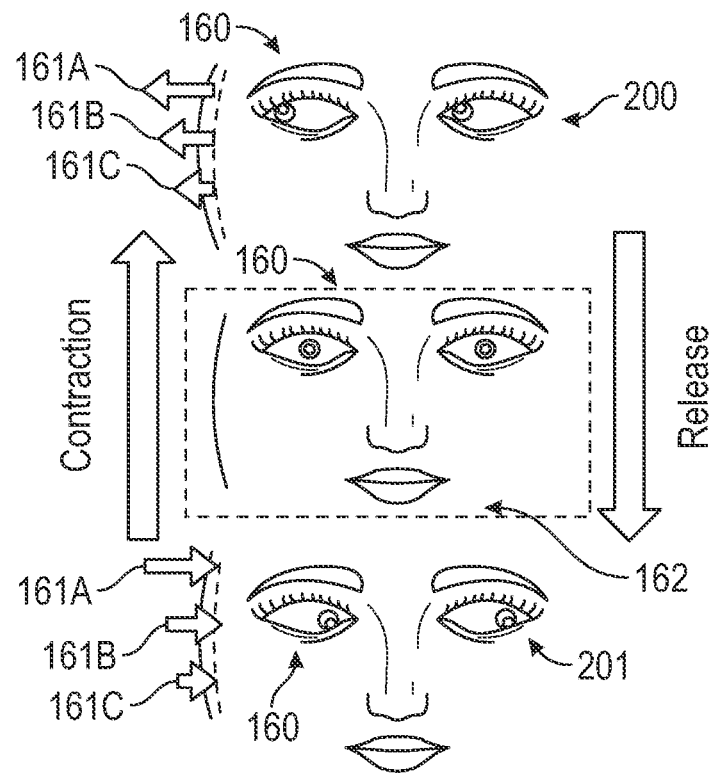
FIGS. 12 and 13 are schematic views of an output voltage response of a plurality of piezoelectric sensors responding to movement of a user's eye.
Figure 13:
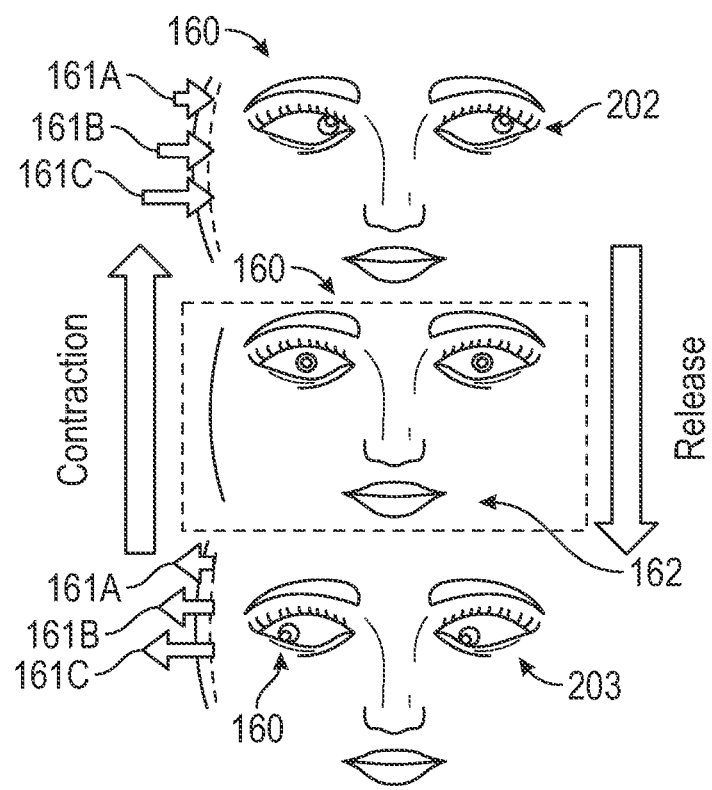

Referring now to FIGS. 1 and 12-27, additional aspects of the operation of eye tracking system 10 are illustrated schematically in FIGS. 12-27. As described above, eye tracking system 10 may track eye movements that are not either purely lateral (shown in FIG. 4) or purely vertical (as shown in FIG. 5). The tracking of eye movement can be extended to other movements including, for example, diagonal and rotational directions with distinguishable signals from the piezoelectric sensors 100A-100C depending on their position on the face of the user 160. FIGS. 12 and 13 illustrate exemplary electrical voltage signals or outputs 161A-161C for piezoelectric sensors 100A (positioned on upper temple area 4), 100B (positioned on middle temple area 5), and 100C (positioned on lower temple area 6d) in response to the user 160 looking alternatingly between a first diagonal direction (indicated by arrow 200 in FIG. 12) and a second diagonal direction (indicated by arrow 201 in FIG. 12), and the user 160 looking alternatingly between a third diagonal direction (indicated by arrow 202 in FIG. 13) and a fourth diagonal direction (indicated by arrow 203 in FIG. 13). The first diagonal direction 200 is oriented substantially in the direction of upper piezoelectric sensor 100A while the second diagonal direction 201 is oriented substantially opposite of the direction of piezoelectric sensor 100A. Additionally, the third diagonal direction 202 is oriented substantially opposite the direction of lower piezoelectric sensor 100C while the fourth diagonal direction 203 is oriented substantially in the direction of piezoelectric sensor 100C.

Figure 14:
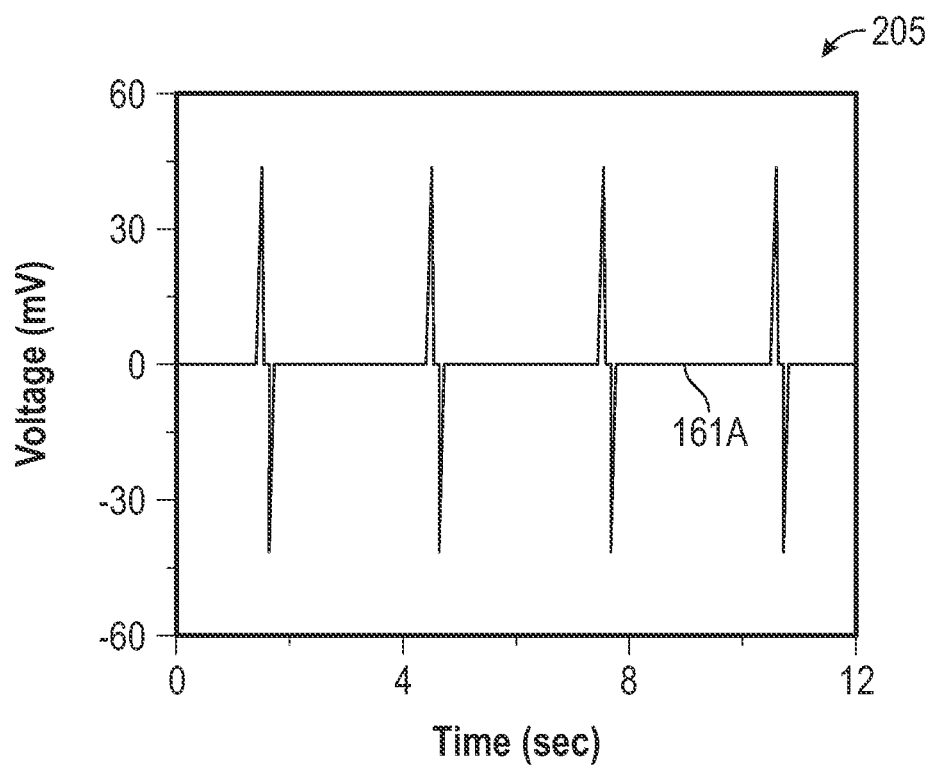
FIG. 14 is a graph illustrating an output voltage of a first piezoelectric sensor of the plurality of piezoelectric sensors of FIG. 12 as a function of time.
Figure 15:
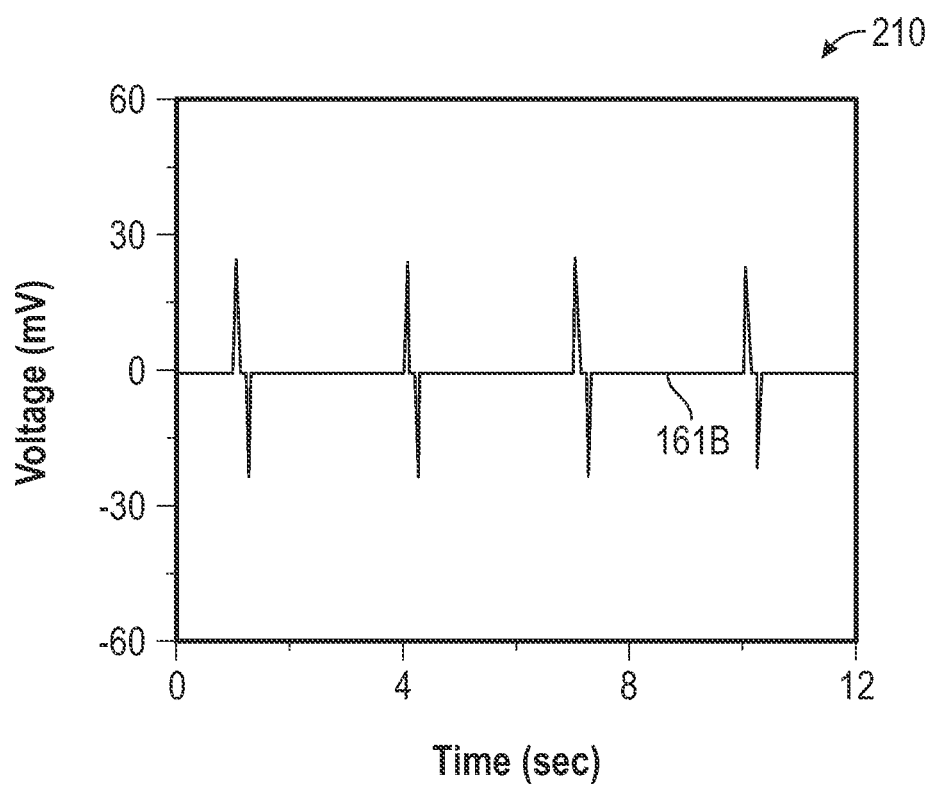
FIG. 15 is a graph illustrating an output voltage of a second piezoelectric sensor of the plurality of piezoelectric sensors of FIG. 12 as a function of time.
Figure 16:
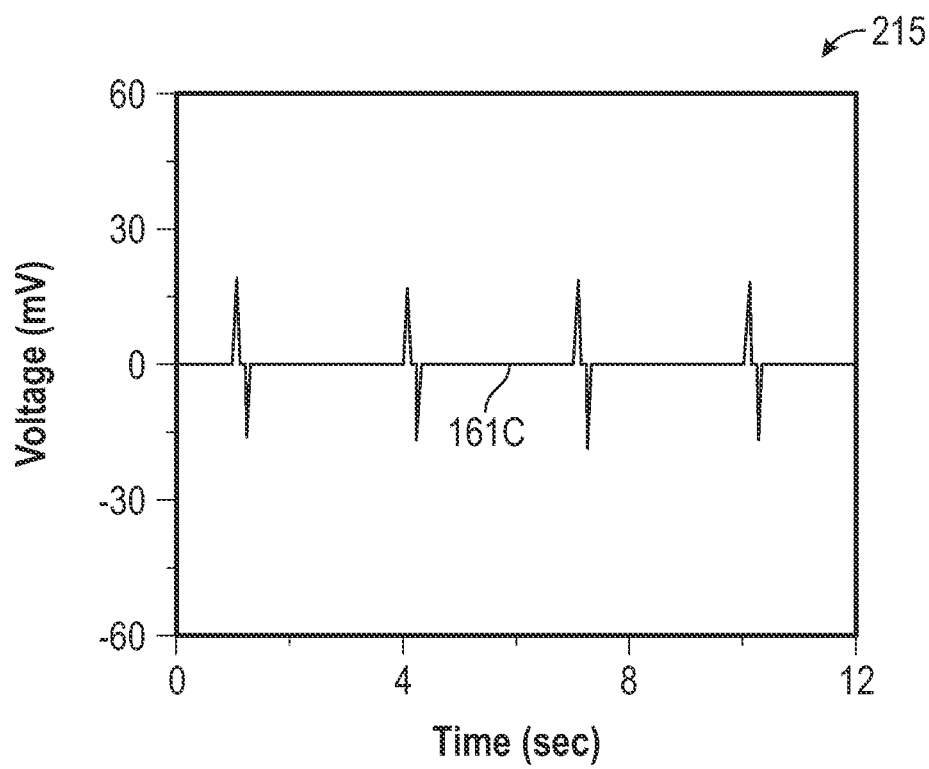
FIG. 16 is a graph illustrating an output voltage of a third piezoelectric sensor of the plurality of piezoelectric sensors of FIG. 12 as a function of time.

Graphs 205, 210, and 215 shown in FIGS. 14-16, respectively, illustrate voltage output 161A (graph 205), voltage output 161B (graph 210), and voltage output 161C (graph 215) as the user 160 looks alternatingly in the first and second diagonal directions 200 and 201, respectively. As shown by graphs 205, 210, and 25, with upper piezoelectric sensor 100A most closely aligned with the direction of travel of the user's eye, the voltage output 161A of upper sensor 100A has both the greatest positive and negative peaks while lower piezoelectric sensor 100C, which is most offset from the direction of travel of the user's eye, has the smallest positive and negative peaks.

Figure 17:
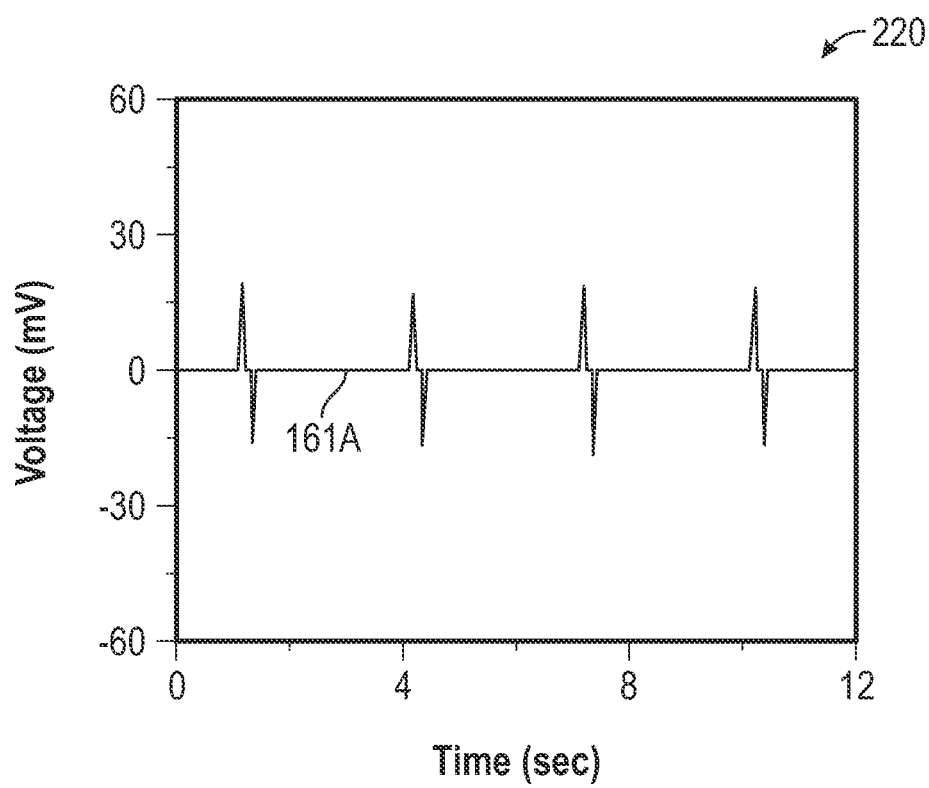
FIG. 17 is a graph illustrating an output voltage of a first piezoelectric sensor of the plurality of piezoelectric sensors of FIG. 13 as a function of time.
Figure 18:
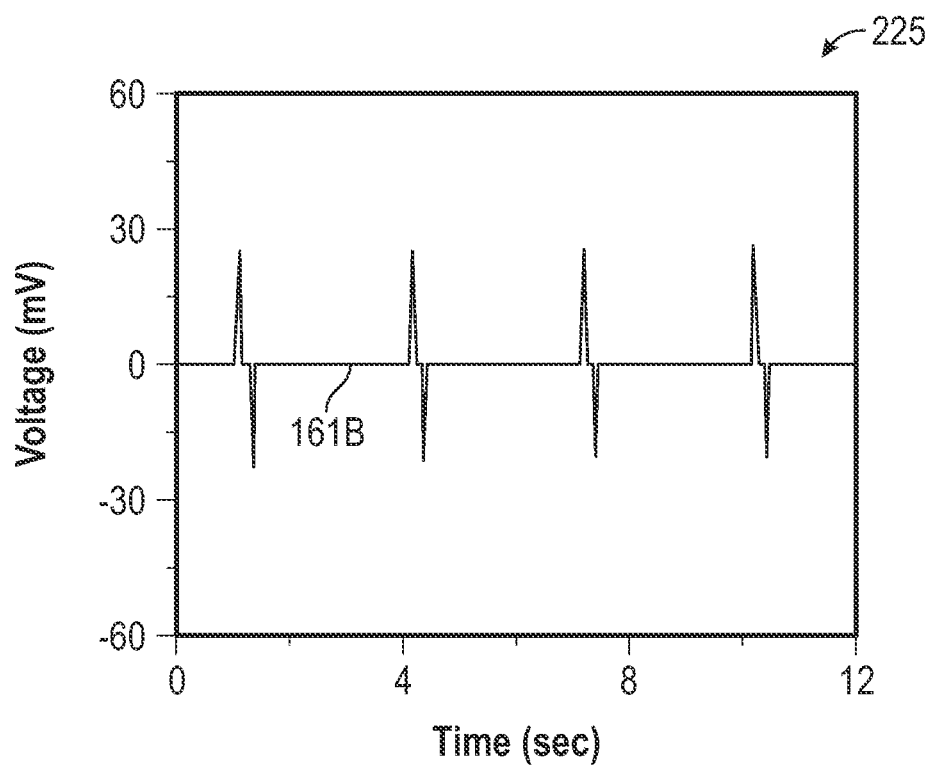
FIG. 18 is a graph illustrating an output voltage of a second piezoelectric sensor of the plurality of piezoelectric sensors of FIG. 13 as a function of time.
Figure 19:
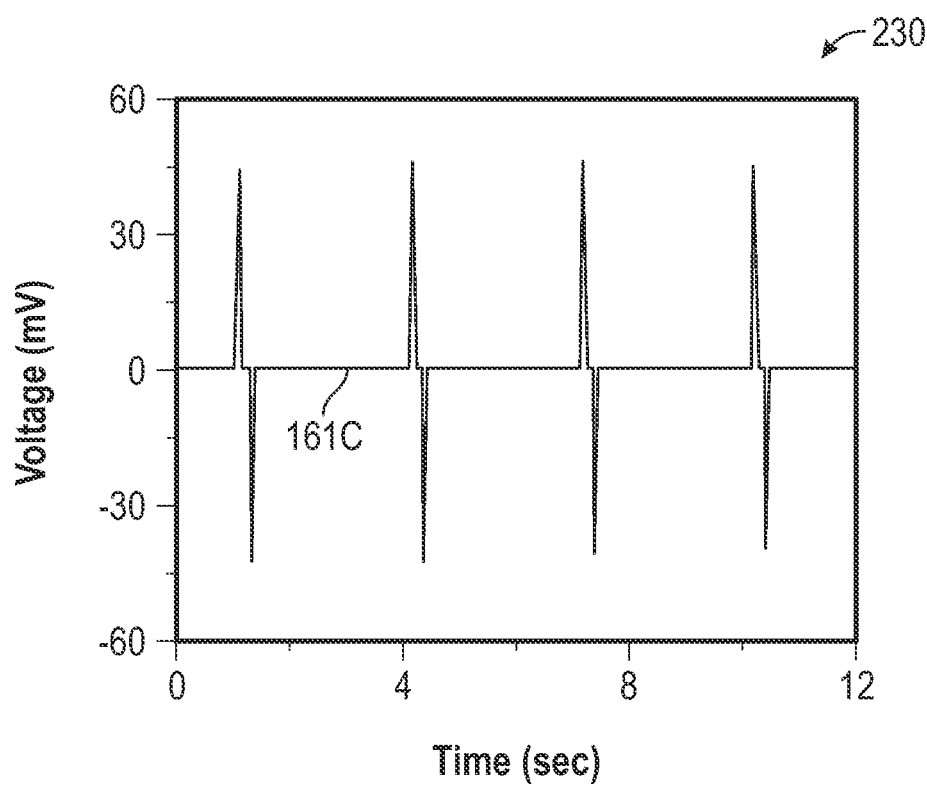
FIG. 19 is a graph illustrating an output voltage of a third piezoelectric sensor of the plurality of piezoelectric sensors of FIG. 13 as a function of time.

Graphs 220, 225, and 230 shown in FIGS. 17-19, respectively, illustrate voltage output 161A (graph 220), voltage output 161B (graph 225), and voltage output 161C (graph 230) as the user 160 looks alternatingly in the third and fourth diagonal directions 202 and 203, respectively. As opposed to graphs 205, 210, and 215 of FIGS. 14-16, graphs 220, 225, and 230 of FIGS. 17-19 illustrate that the voltage output 161C of the lower piezoelectric sensor 100C, which is most closely aligned to the direction of travel of the user's eye in the third and fourth directions 202 and 203, has both the greatest positive and negative peaks. Conversely, the voltage output 161A of the upper piezoelectric sensor 100A, which is farthest offset from the third and fourth directions 202 and 203, has the smallest positive and negative peaks.

Figure 20:
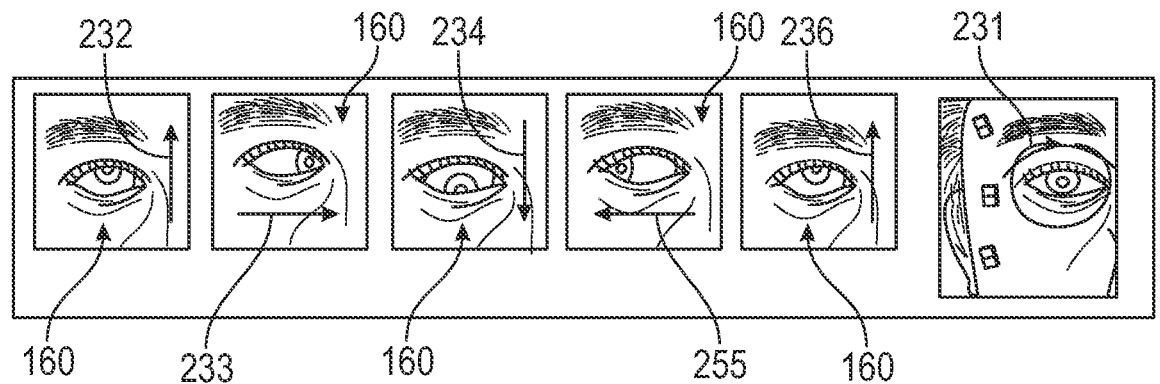
FIG. 20 is a schematic view of an output voltage response of a plurality of piezoelectric sensors responding to movement of a user's eye.
Figure 21:
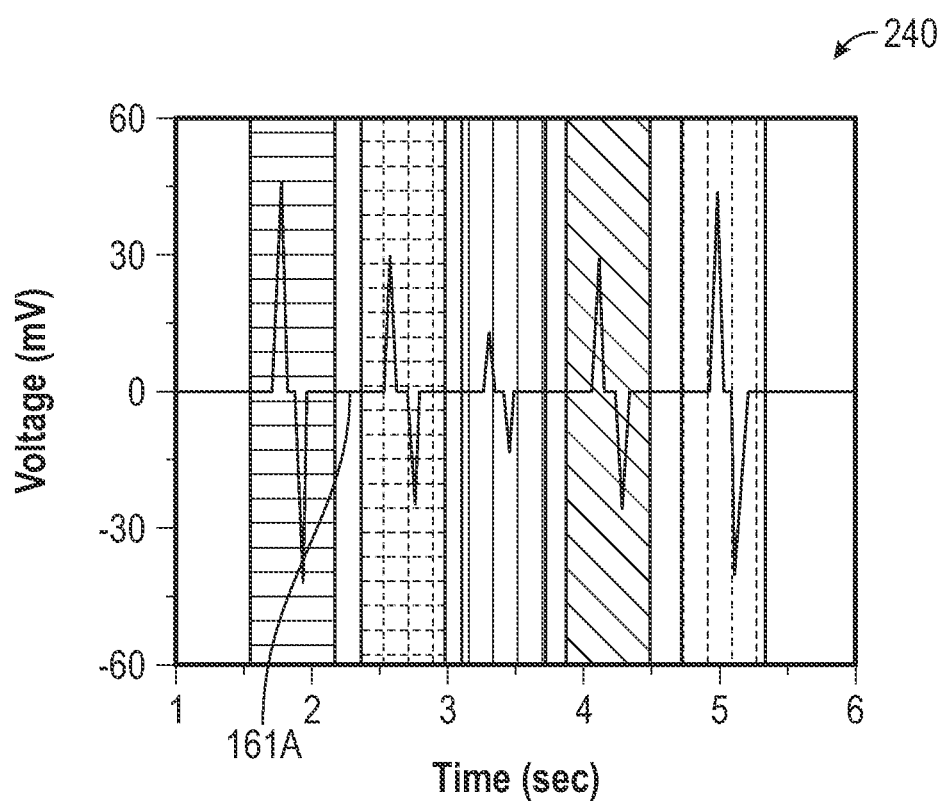
FIG. 21 is a graph illustrating an output voltage of a first piezoelectric sensor of the plurality of piezoelectric sensors of FIG. 20 as a function of time.
Figure 22:
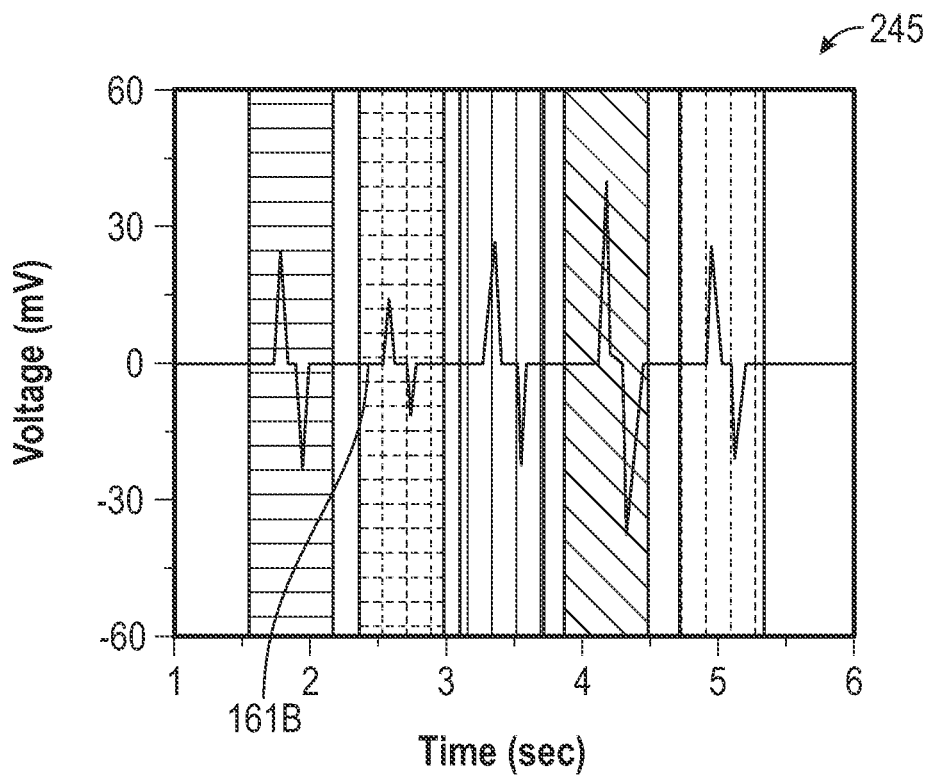
FIG. 22 is a graph illustrating an output voltage of a second piezoelectric sensor of the plurality of piezoelectric sensors of FIG. 20 as a function of time.
Figure 23:
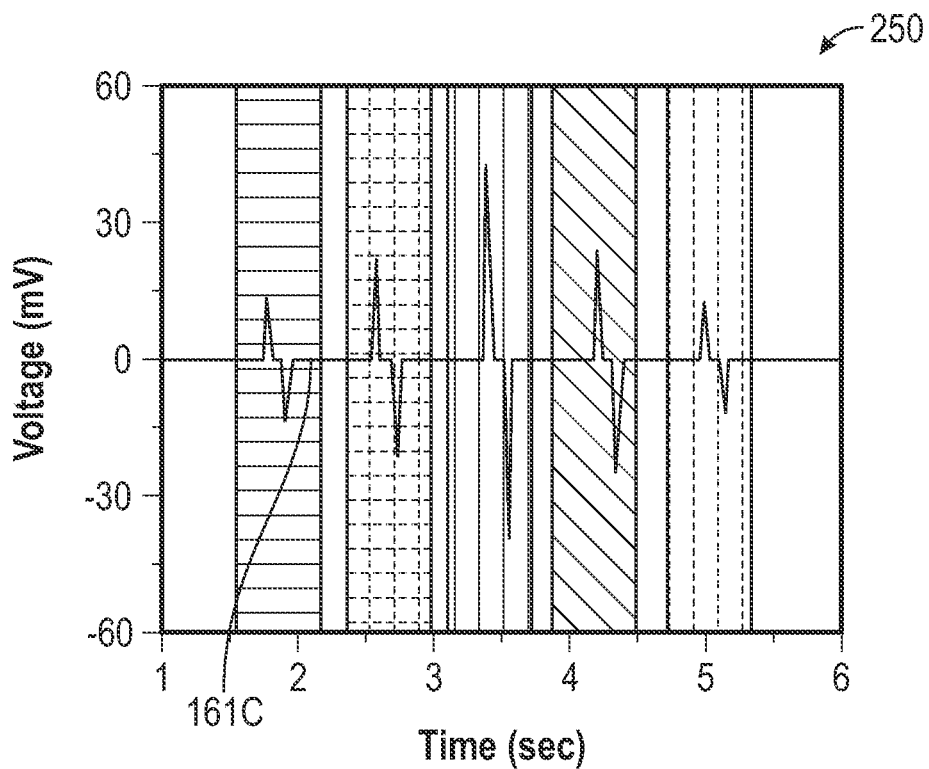
FIG. 23 is a graph illustrating an output voltage of a third piezoelectric sensor of the plurality of piezoelectric sensors of FIG. 20 as a function of time.

FIG. 20 illustrates the user 160 rotating their eye in a first (clockwise) rotational direction (indicated by arrow 231). This rotational movement is broken down into a sequential series of steps or directional movements (indicated by arrows 232-236) also indicated in FIG. 20. These steps 232-236 are captured in graphs 240, 245, and 250 shown in FIGS. 21-23, respectively. Particularly, graph 240 indicates voltage output 161A of upper piezoelectric sensor 100A; graph 245 indicates voltage output 161B of middle piezoelectric sensor 100B, and graph 250 indicates voltage output 161C of lower piezoelectric sensor 100C as the user 160 moves his eye in the first rotational direction 231. As shown in graphs 240, 245, and 250, each voltage output 161A-161C has a series of positive and negative peaks which vary as the direction of the travel of the user's eye varies along steps 232-236, where the degree of offset (from the direction of travel) and proximity between the sensor 100A-100C and the then current position of the user's eye correlates with the magnitude of the given positive or negative peak.

Figure 24:
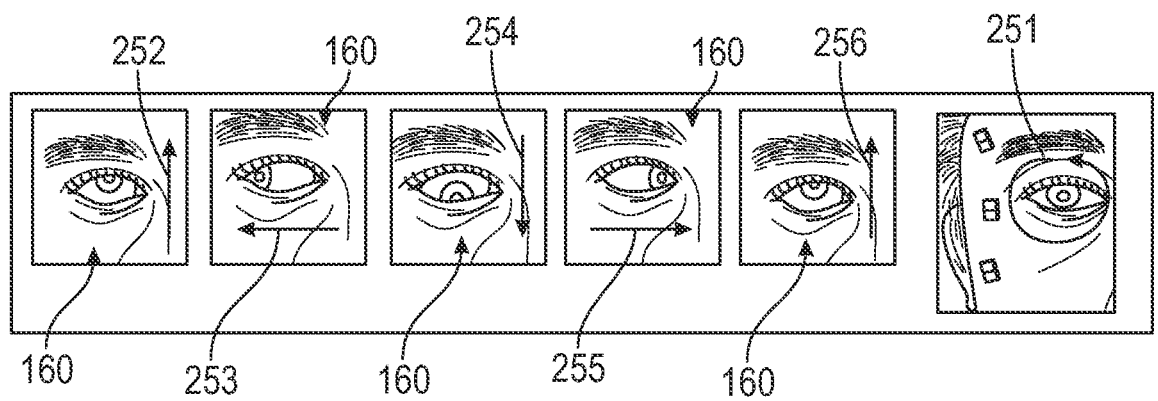
FIG. 24 is a schematic view of an output voltage response of a plurality of piezoelectric sensors responding to movement of a user's eye.
Figure 25:
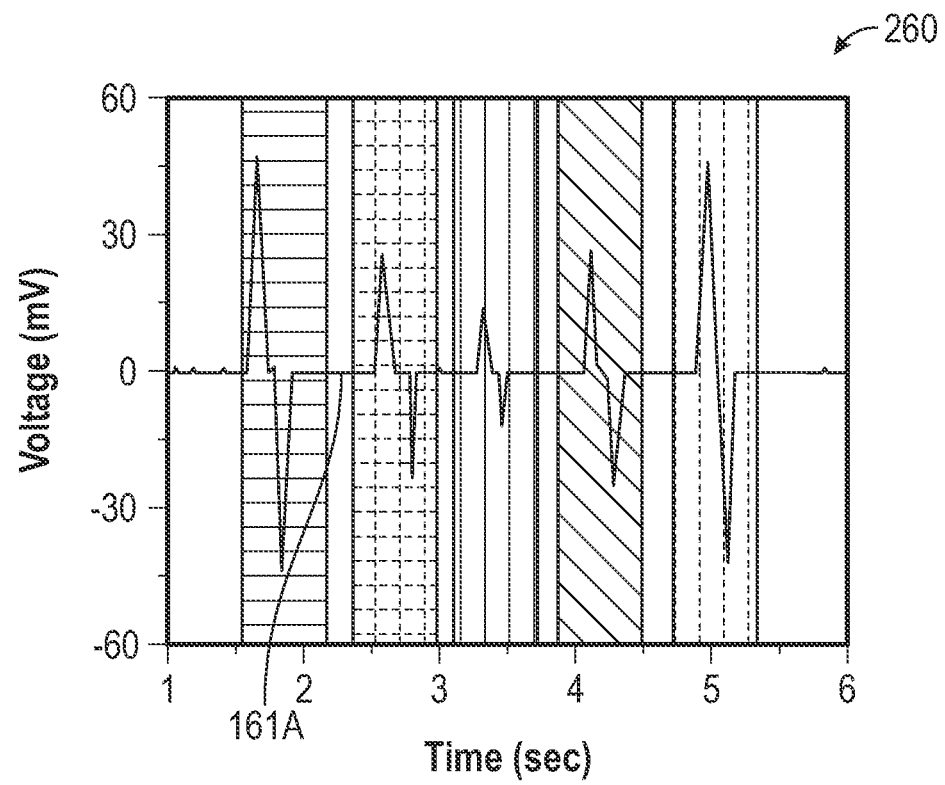
FIG. 25 is a graph illustrating an output voltage of a first piezoelectric sensor of the plurality of piezoelectric sensors of FIG. 24 as a function of time.
Figure 26:
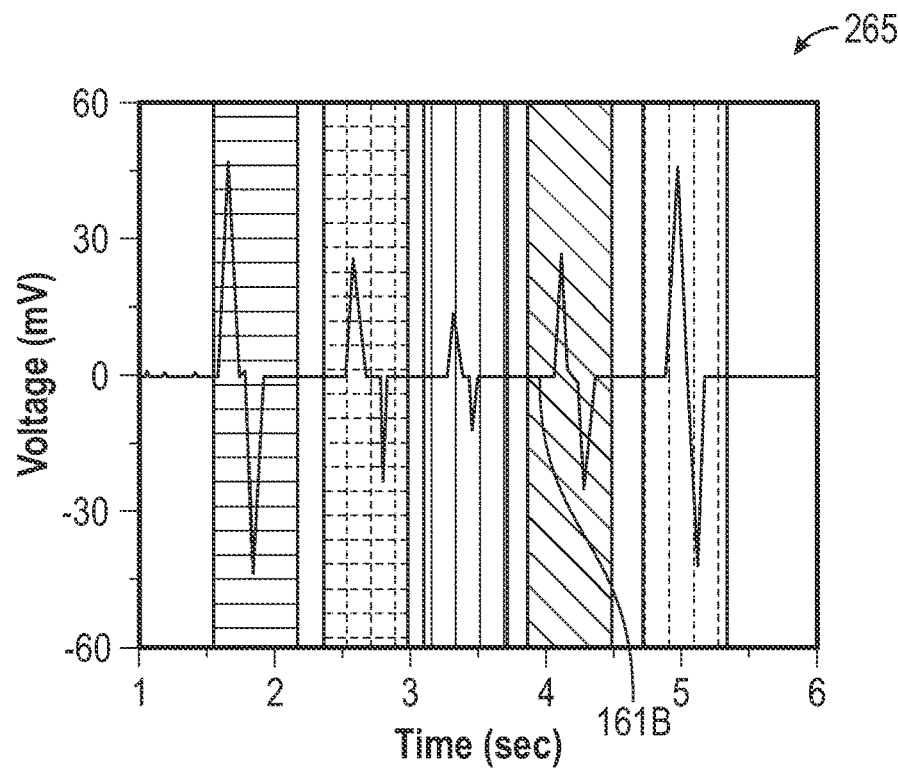
FIG. 26 is a graph illustrating an output voltage of a second piezoelectric sensor of the plurality of piezoelectric sensors of FIG. 24 as a function of time.
Figure 27:
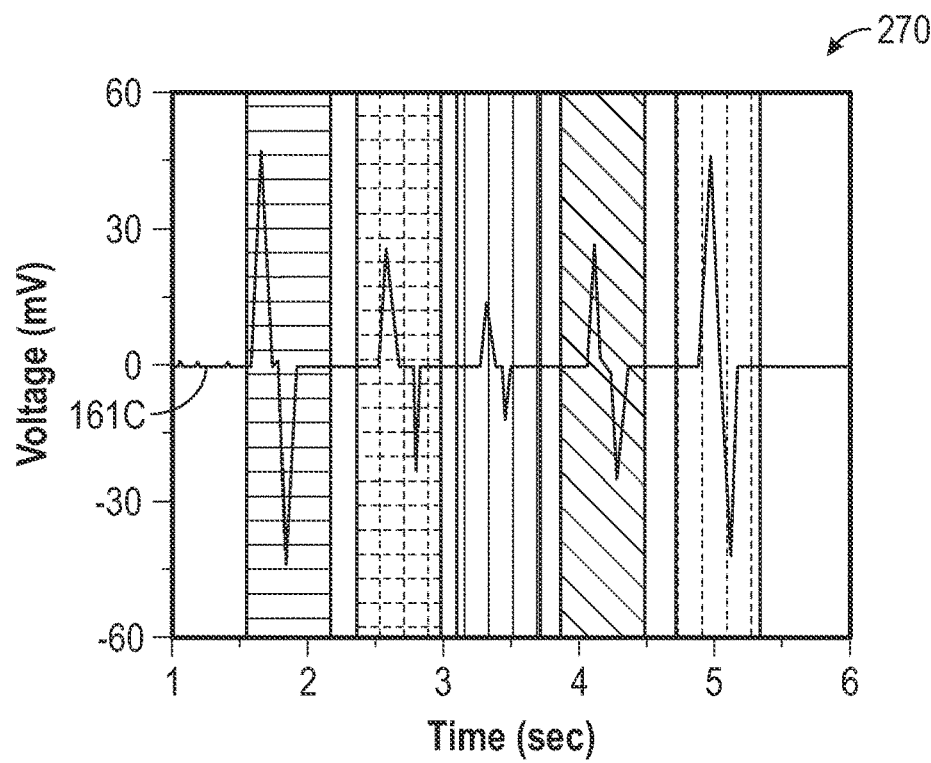
FIG. 27 is a graph illustrating an output voltage of a third piezoelectric sensor of the plurality of piezoelectric sensors of FIG. 24 as a function of time.

FIG. 24 illustrates the user 160 rotating their eye in a second (counterclockwise) rotational direction (indicated by arrow 251) that is opposite the first rotational direction 231. This rotational movement is broken down into a sequential series of steps or directional movements (indicated by arrows 252-256) also indicated in FIG. 24. These steps 252-256 are captured in graphs 260, 265, and 260 shown in FIGS. 25-27, respectively. Particularly, graph 260 indicates voltage output 161A of upper piezoelectric sensor 100A; graph 265 indicates voltage output 161B of middle piezoelectric sensor 100B, and graph 270 indicates voltage output 161C of lower piezoelectric sensor 100C as the user 160 moves his eye in the second rotational direction 251. Similar to graphs 240, 245, and 250 described above, as shown in graphs 260, 265, and 270, each voltage output 161A-161C has a series of positive and negative peaks which vary as the direction of the travel of the user's eye varies along steps 252-256.

Figure 28:
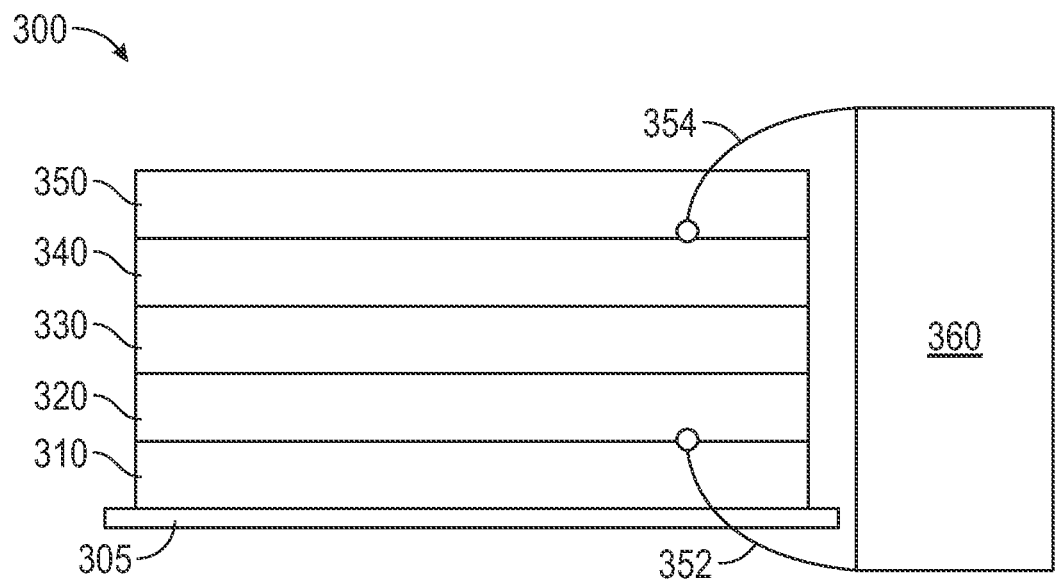
FIG. 28 is a schematic side view of an embodiment of a flexible piezoelectric sensor.

Referring now to FIG. 28, an embodiment of a flexible skin-attachable piezoelectric sensor 300. Piezoelectric sensors 100A-100C of eye tracking system 10 may each be configured similarly as the piezoelectric sensor 300 described below. However, the configuration of the sensors 100A-100C of eye tracking system 10 may vary in other embodiments. The piezoelectric sensor 300 may be comfortably won on the face of a user, such as the temple area of the user.

In this exemplary embodiment, piezoelectric sensor 300 generally includes a pair of electrically insulative layers or insulators 310 and 350, a pair of electrically conductive layers or electrodes 320 and 340, a piezoelectric layer or film 330. The piezoelectric film 330 is sandwiched between the pair of electrodes 320 and 340. Similarly, the pair of electrodes are sandwiched between the pair of insulators 310 and 350. Piezoelectric sensor 300 also comprises an attachment pad or layer 305 configured to flexibly attach the piezoelectric sensor 300 to the face of a user such that the sensor 300 may be worn comfortably on the user's face, removed, and reattached to the user's face as needed. In some embodiments, attachment pad 305 comprises an adhesive pad meant to temporarily adhere to the user's face.

The piezoelectric sensor 300 additionally includes a pair of signal conductors 352 and 354 connected to the electrodes 320 and 340, and a wireless transmitter 360 connected to the pair of signal conductors 352 and 354. Electrodes 352 and 354 produce a voltage output (e.g., voltage outputs 161A, 161B, and 161C) in response to flexure of the piezoelectric film 330. Wireless transmitter 360 is configured to transmit a signal corresponding to the voltage produced by signal conductors 352 and 354 to a computer system (e.g., computer system 20 shown in FIG. 1). While in this exemplary embodiment piezoelectric sensor 300 is configured for wireless communication via wireless transmitter 360, in other embodiments, piezoelectric sensor 300 may communicate to the computer system through a wired connection and thus may not include wireless transmitter 360. It may also be understood that piezoelectric sensor 300 may include features in addition to those shown in FIG. 28.

The piezoelectric film 330 is flexible and does not comprise any toxic materials such as lead. Additionally, piezoelectric film 330 is highly sensitive to provide piezoelectric sensor 300 with sensitivity required to detect eye movement and position as described above with respect to eye tracking system 10. In this exemplary embodiment, piezoelectric film 330 comprises a Gallium-Nitride-based or Gallium-Nitride-comprising material. Gallium Nitride provides a nontoxic alternative to other substances such as lead, permitting the piezoelectric sensor 300 to be safely worn on the face of the user.

As will be described further herein, the piezoelectric film 330 comprises a defectless Gallium Nitride material in which defects or flaws have been intentionally removed from the Gallium Nitride material as part of forming the piezoelectric film 330 and sensor 300. Particularly, in some embodiments, microcracks and other flaws are removed from the Gallium Nitride material as part of forming of the piezoelectric film 330. In some embodiments, each of four edges of the Gallium Nitride material, which may contain cracks and irregular saw-tooth edges, are etched with a depth more than thickness of the Gallium Nitride film. In some embodiments, after removal of the edges, a remaining sidewall of the Gallium Nitride film defining an outer perimeter of the film has a surface roughness that is 500 micrometers ($\mu$m) or less as measured from the difference between the peaks and valleys of the sidewall of the Gallium Nitride film. Gallium Nitride is traditionally a relatively brittle material, particularly when compared with relatively flexible materials like lead used in applications in which the piezoelectric sensor must be relatively flexible. However, the lack of deflects or flaws in piezoelectric film 330 provides the piezoelectric film 330 with the flexibility required to be worn on an uneven, dynamic surface such as a user's face.

In addition to being more flexible than traditional Gallium Nitride materials, the Gallium Nitride film material comprising piezoelectric film 330 also has a greater sensitivity than conventional Gallium Nitride materials. For example, in some embodiments, piezoelectric film 330 has a sensitivity ranging approximately between 0.1 volts per newton (V/N) and 5 V/N. In certain embodiments, the sensitivity of piezoelectric film 330 is approximately between 0.1 V/N and 1.0 V/N. In some embodiments, the piezoelectric film 330 comprises a Gallium Nitride material having a single-crystalline structure in which there are no grain boundaries and instead the crystal lattice extends unbroken to the edges of the film 330. For example, in some embodiments, the piezoelectric film 330 comprises a group III-nitride (III-N) thin film with a single-crystalline structure. In some embodiments, the piezoelectric film 330 comprises at least one of aluminum nitride (AlN), gallium nitride (GaN), scandium nitride (ScN), indium nitride (InN), and combinations of these materials. In certain embodiments, piezoelectric film 330 comprises a plurality of separate and distinct layers of III-N thin films including AlN, GaN, InN, and their alloys in accordance with the formula of $In_xAl_ySc_zGa_{1-x-y-z}N$ (where $0 \leq x \leq 1$, $0 \leq y \leq 1$, and $0 \leq z \leq 1$). In certain embodiments, piezoelectric film 330 has a thickness of approximately between one nanometer (nm) and one millimeter (mm); however, it may be understood that the thickness of piezoelectric film 330 may vary in other embodiments. It may also be understood that the materials comprising piezoelectric film 330 may vary depending on the given embodiment. For example, in some embodiments, piezoelectric film 330 may not include a Gallium Nitride material.

Figure 29:
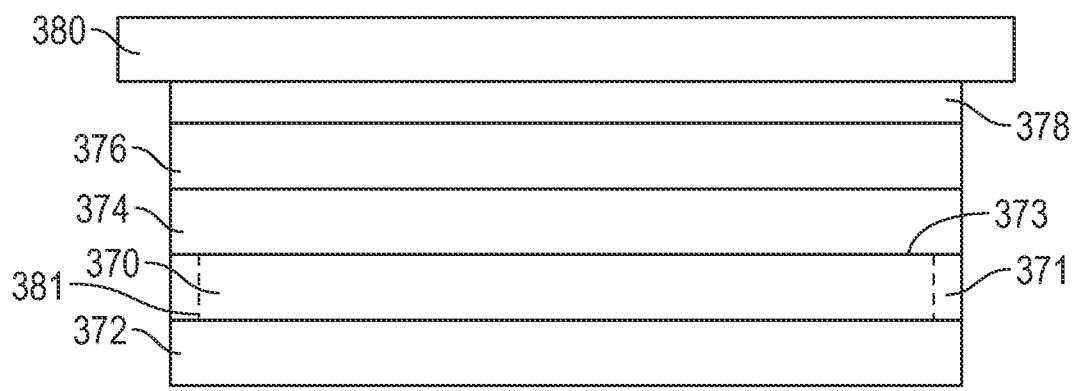
FIGS. 29-31 are schematic side views of an exemplary process for forming a flexible piezoelectric sensor.
Figure 30:
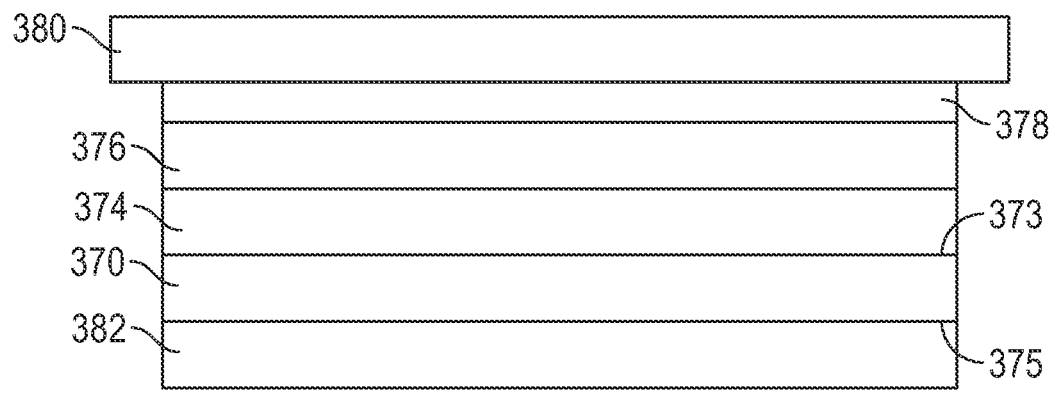
Figure 31:
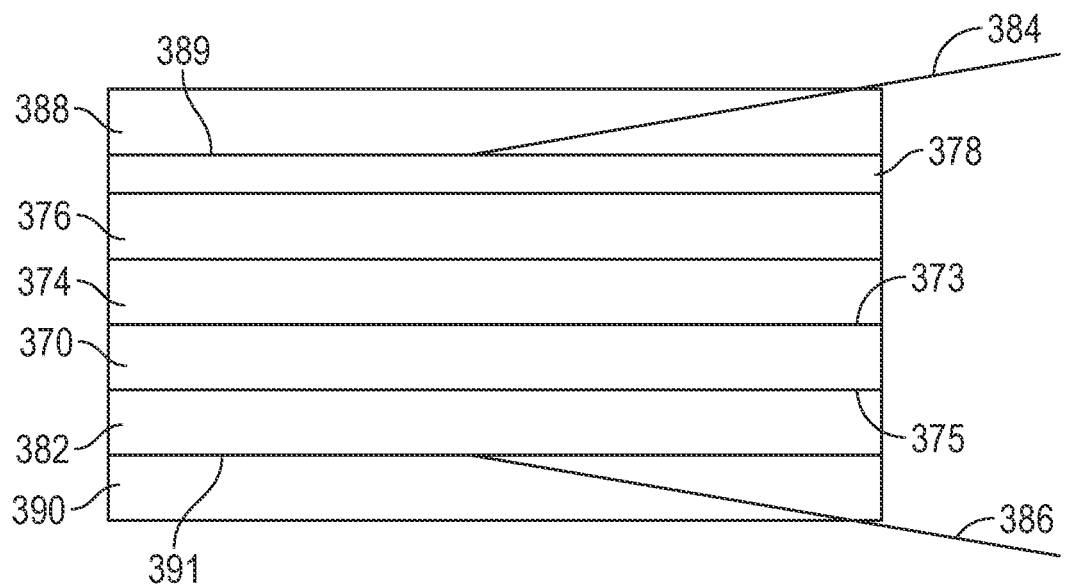

Referring to FIGS. 29-31, an exemplary process for forming a flexible, skin-attachable piezoelectric sensor such as the piezoelectric sensor 300 is shown. In this exemplary embodiment, a single-crystalline thin film 370 (e.g., a III-N thin film) is grown epitaxially in a substrate 372 as shown in FIG. 29. In some embodiments, during or following the growth of thin film 370 on the substrate 372, an outer perimeter or edge 371 of the thin film 370 is detached and removed from the thin film 370. Particularly, the entire outer edge 371 extending about the entire perimeter of the thin film 370 may be removed. Microcracks may form in the outer edge 371 of thin film 370 following the growth of film 370 on the substrate 372. For example, in some embodiments, thin film 370 is cut into a plurality of samples following growth where the cutting process may form microcracks or other forms of damage along the outer edges 371 of the thin film 370. If left attached to the thin film 370, the microcracks formed in the outer edge 371 thereof may propagate through the thin film 370 as stresses are applied to the thin film 370, limiting the durability and performance of the thin film 370 during operation of the piezoelectric sensor comprising the film 370. In some embodiments, the outer edge 371 removed from the thin film 370 is approximately 2.0 mm or less in width. An exterior or outer sidewall 381 of the thin film 370 remaining following the removal of outer edge 371 may have a maximum or an average surface roughness that is 500 μm or less. In some embodiments, the surface roughness of outer sidewall 381 is 300 μm or less. In some embodiments, the surface roughness of outer sidewall 381 is 100 μm or less. Additionally, in certain embodiments, the thin film 370 may be analyzed (e.g., using an optical microscope) before and/or following the removal of outer edge 371 to confirm the removal of the microcracks from the thin film 370 prior to the completion of the process for forming a piezoelectric sensor from the thin film 370.

In some embodiments, substrate 372 comprises one or more of silicon (Si), sapphire, and Silicon Carbide (SiC). Following or as the thin film 370 is grown, a first or upper electrode layer 374 is deposited onto a top or upper surface 373 of the thin film 370. The upper electrode layer 374 comprises an electrode formed from an electrically conductive material such as nickel, titanium, and gold. Following the deposition of upper electrode layer 374, a transition layer 376 is deposited onto the electrode 374. Transition layer 376 also comprises an electrically conductive material such as nickel or copper. In some embodiments, transition layer 376 is deposited onto upper electrode layer 374 by electroplating with a thickness ranging approximately between tens and hundreds of μm.

In this exemplary embodiment, a protection layer 378 is deposited onto the transition layer 376. Protection layer 378 comprises a noble metal such as gold Additionally, an output of the assembly of layers is attached to a wafer 380. In some embodiments, wafer 380 comprises a chemically stable material such as sapphire, and the wafer 380 may be attached to the protection layer 378 via an adhesive such as polymeric glue. Following the assembly of the layers (e.g., layers 370, 374, 376, and 378), the substrate 372 is removed using a microfabrication removal process such as a wet-etching process, a dry-etching process, and a laser-liftoff process.

As shown particularly in FIG. 30, following the removal of substrate 372, a second or lower electrode layer 382 is deposited onto the now exposed bottom or lower surface 375 of the thin film 370. The lower electrode layer 382 comprises an electrode formed from an electrically conductive material such as nickel, titanium, and gold. Additionally, the wafer 380 is detached and removed from the protection layer 378. Further, a pair of signal conductors or wires 384 and 386 are connected to the electrode layers 374 and 382, respectively, as shown in FIG. 31. In this arrangement, first or upper wire 384 is electrically connected to the upper electrode layer 374 while the second or lower wire 386 is electrically connected to the lower electrode layer 382. Following the connection of wires 384 and 386 to layers 374 and 382, a pair of insulating layers 388 and 390 are coated onto a top or upper end 389 and onto a bottom or lower end 391 of the assembly of layers to seal the electrode layers 374 and 382 and thin film 370 from the surrounding environment. In some embodiments, insulating layers 388 and 390 each comprise a Si material such as Polydimethylsiloxane (PDMS).

Figure 32:
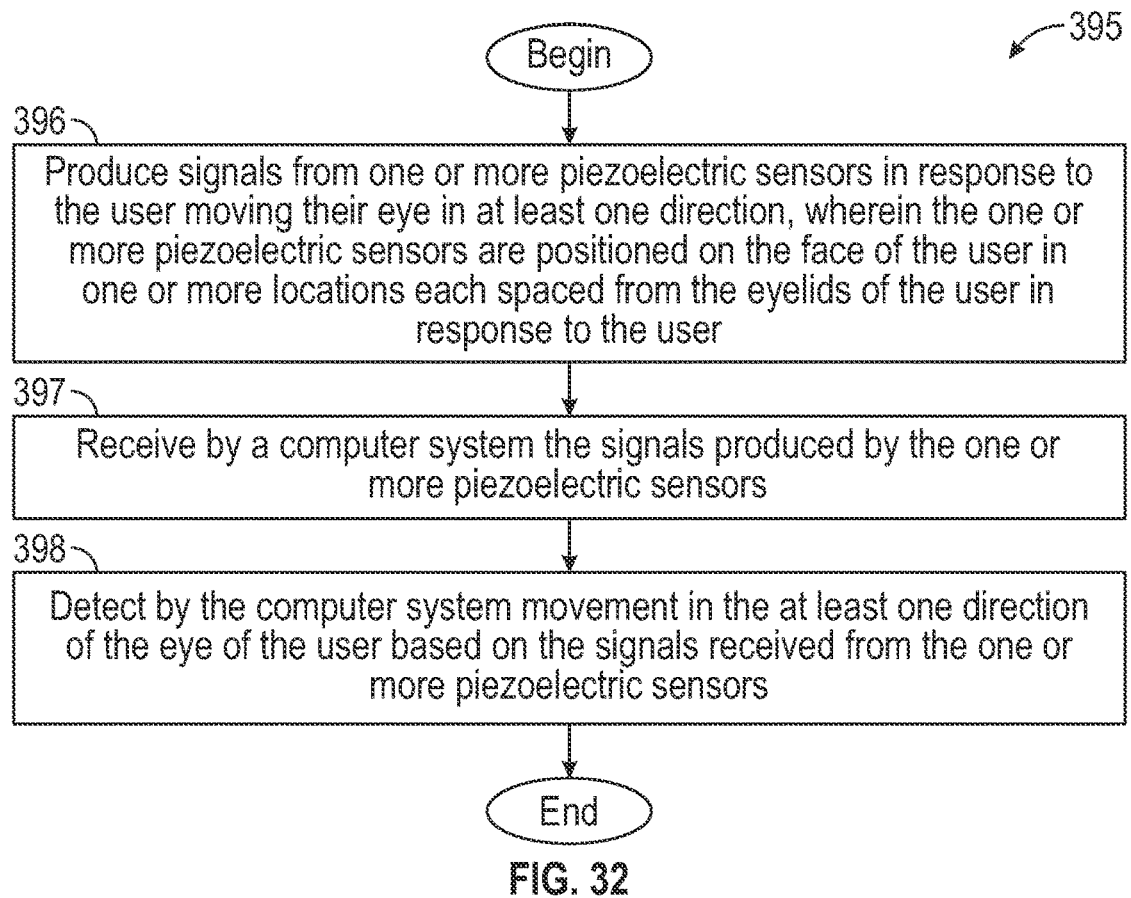
FIG. 32 is a flowchart of an embodiment of a method for tracking an eye of a user.

Referring to FIG. 32, an embodiment of a method 395 for tracking an eye of a user is shown. Initially, block 396 of method 395 includes producing signals from one or more piezoelectric sensors in response to the user moving their eye in at least one direction, wherein the one or more piezoelectric sensors are positioned on the face of the user in one or more locations each spaced from the eyelids of the user in response to the user. In some embodiments, block 396 includes producing signals from piezoelectric sensors 100A-100C of the eye tracking system 10 shown in FIG. 1 in response to the user moving their eye in at least one direction. Block 397 of method 395 includes receiving by a computer system the signals produced by the one or more piezoelectric sensors. In some embodiments, block 397 includes receiving by the computer system 20 shown in FIG. 1 the signals produced by the piezoelectric sensors 100A-100C. Block 398 of method 395 includes detecting by the computer system movement in the at least one direction of the eye of the user based on the signals received from the one or more piezoelectric sensors. In some embodiments, block 398 includes detecting by the computer system 20 movement in the at least one direction of the eye of the user based on the signals received from piezoelectric sensors 100A-100C.

Figure 33:
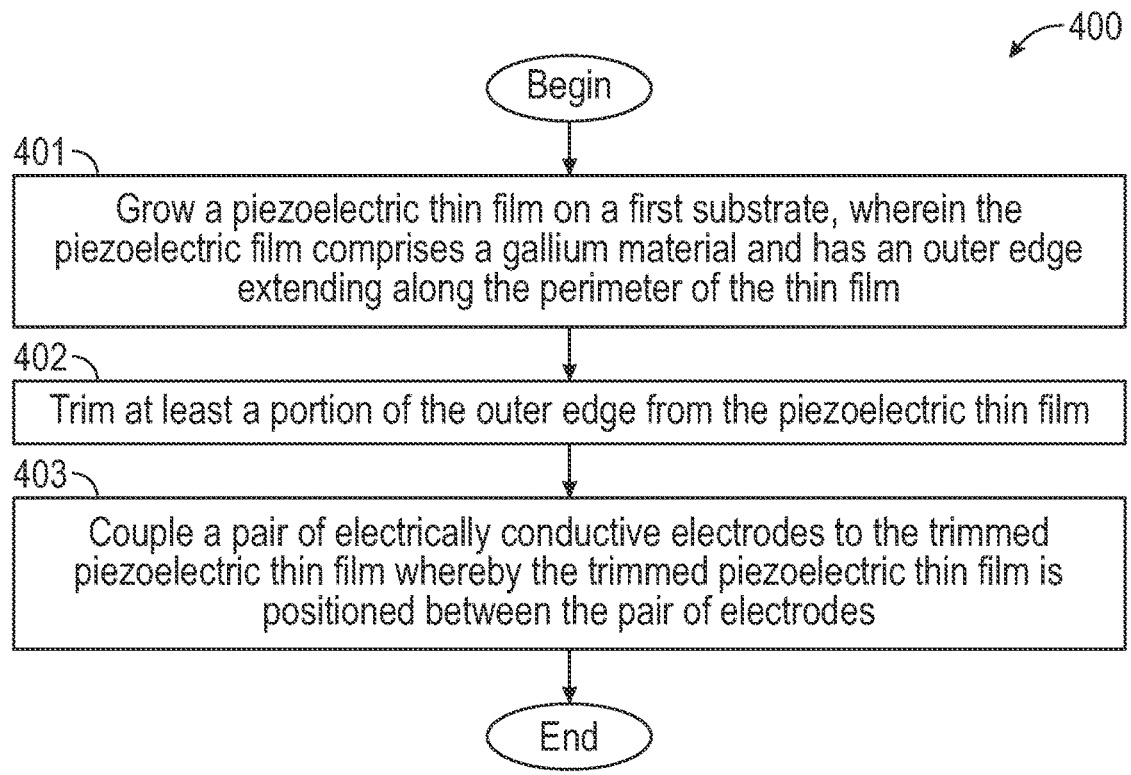
FIG. 33 is a flowchart of an embodiment of a method for forming a flexible piezoelectric sensor.

Referring to FIG. 33, an embodiment of a method 400 for tracking an eye of a user is shown. Initially, block 401 of method 400 includes growing a piezoelectric thin film on a first substrate, wherein the piezoelectric film comprises a Gallium material and has an outer edge extending along the perimeter of the thin film. In some embodiments, block 401 includes growing the piezoelectric film 330 of the piezoelectric sensor 300 shown in FIG. 28. Block 402 of method 400 includes trimming at least a portion of the outer edge from the piezoelectric thin film. In some embodiments, block 402 includes trimming at least a portion of the outer edge from the piezoelectric film 330. Block 403 of method 400 includes coupling a pair of electrically conductive electrodes to the trimmed piezoelectric thin film whereby the trimmed piezoelectric thin film is positioned between the pair of electrodes. In some embodiments, block 403 includes coupling the pair of electrodes 320 and 340 shown in FIG. 28 to the trimmed piezoelectric film 330.

Experiments were conducted regarding both flexible, skin-attachable piezoelectric sensors and systems for tracking the position and movement of a user's eye using one or more piezoelectric sensors. It may be understood that the following experiments described herein are not intended to limit the scope of this disclosure and upon the embodiments described above and shown in FIGS. 1-33.

In previous studies, strain sensors have been used to indirectly detect the movement of eyes by attaching them directly on the eyelid. The piezoelectric strain sensors based on lead zirconate titanate ($Pb[Zr_xTi_{1-x}]O_3$, PZT) and zinc oxide (ZnO) were able to measure the strain change on the eyelids upon their moving; however, they showed limitations as a wearable and reliable sensor. Particularly, PZT contains a significant amount of harmful lead, which causes poisoning in the human body. Wearable and implantable sensors should generally be toxic-element-free. Additionally, ZnO sensor showed low sensitivity and resolution, which requires additional signal processing of amplification and noise reduction. The benefit of non-toxicity of ZnO cannot compensate for low sensing performance, the most fundamental function of the sensors. Most importantly, all the previous sensors were attached directly on the eyelid where the most pronounced output signals from the surface strain change can be obtained at the expense of comfort and safety of the user. For at least this reason, the previous sensors are not truly noninvasive for safe and comfortable wearing.

Alternative piezoelectric sensing elements have been sought for in healthcare monitoring systems to replace safety-hazard-ridden PZT sensors while achieving high electromechanical coupling factors comparable to PZT. The current study investigates single-crystalline group III-N materials, especially gallium nitride (GaN) thin films, which have the potential for excellent piezoelectric sensing and energy-harvesting with many advantageous electrical, mechanical, and chemical properties. GaN thin films, naturally formed permanent electric dipoles are already aligned in one direction, hence, electrical poling process is not required to obtain piezoelectric property, which is different from PZT. Additionally, GaN is chemically and thermally stable and generally safe on human skin and in the body. Further, GaN is stable and does not react with skin and body fluid. The biocompatibility of GaN makes it a prime candidate to overcome the critical limitation of PZT in epidemic and implantable sensors and electronics. Moreover, GaN thin films on flexible substrates showed excellent mechanical bendability and durability without degradation in materials and output characteristics of the devices, which provides an important benefit for reliable and continuous monitoring of the sensor. This characteristic is somewhat surprising considering the brittle nature of its bulk material; however, the durability and bendability of the film have been experimentally confirmed as part of this study. Most importantly, GaN has a relatively high electromechanical coupling coefficient due to its low dielectric constant. Single-crystalline GaN thin films are indicated by this study as exhibiting high performance in pressure sensing (output value, sensitivity, response time, and stability).

In the present study, the operating principles and characteristics of the sensor for eye blinking and eyeball motions were investigated. The output signals generated by the sensor due to eye motion were numerically estimated, experimentally measured, and analyzed at various positions (upper eyelid, lower eyelid, and temple). As a result, it was demonstrated for the first time that an eye movement sensor attached on a temple area of the face is capable of accurately measuring various movements of eyes for noninvasive and reliable sensing in many extended applications.

Sensor Design and Fabrication

Figure 34:
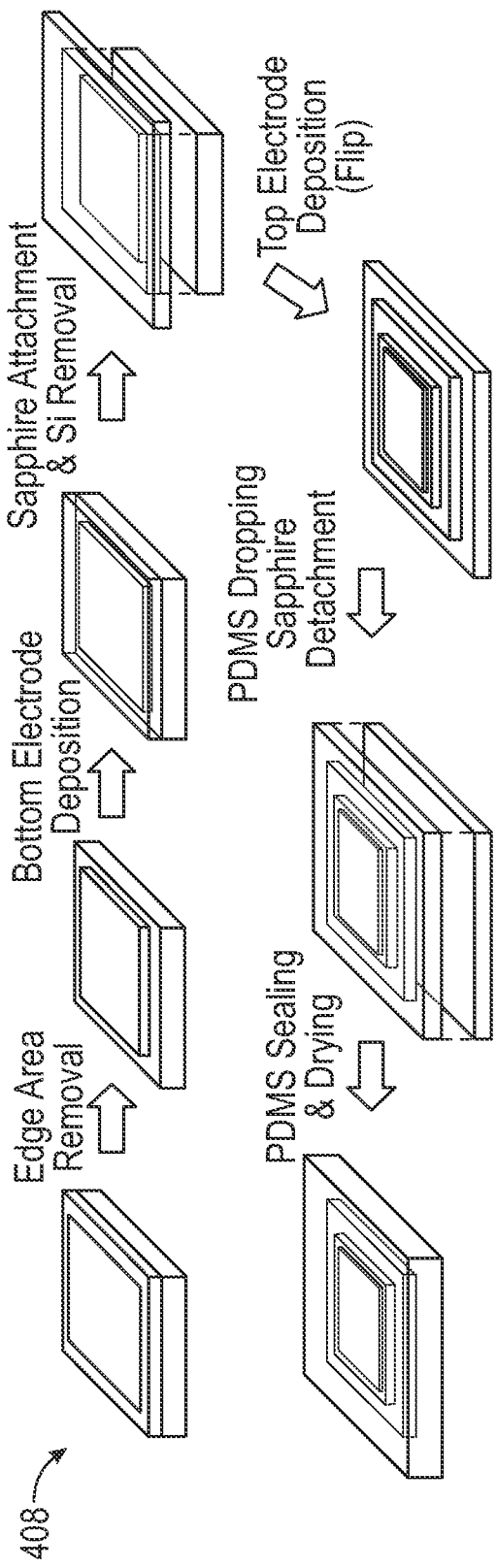
FIG. 34 is a schematic view of an exemplary process for forming a flexible piezoelectric sensor.

Referring now to FIG. 34, a process 408 is shown for fabricating flexible piezoelectric eye-movement sensors (F-PEMS). An edge area within ~1 mm from the edge of the III-N thin films comprising the F-PEMS were removed. These edge areas were damaged during the dicing process. Microcracks existing in the edge area could be propagated by mechanical stresses during the handling, attachment, and operation of the sensor, potentially resulting in the degradation of sensor performance. Enhanced reliability and durability of the sensor could be achieved by this process step. Optical microscope images of as-diced and edge-removed samples of GaN on Si confirmed that microcracks in the edges within several hundred micrometers no longer existed after the edge removal. Then, an electrode comprising a stack of nickel, gold, copper, and gold (Ni/Au/Cu/Au) metal layers was deposited on top of the III-N thin-film surface, which became a bottom electrode after the flip of the sample for further fabrication. A sapphire substrate was bonded to the electrode of the sample and the Si substrate was etched. Then, the sapphire was detached from the sample. After removing the Si and sapphire substrates, the sample was flipped and a top electrode with Ni/Au was deposited to complete the fabrication of the sensor element. Finally, the device was sealed by polydimethylsiloxane (PDMS) with wires attached to the electrodes. The top and bottom electrodes became anode and cathode, respectively.

Figure 35:
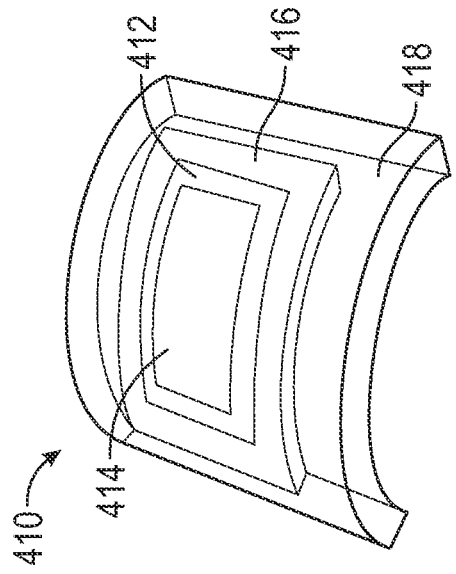
FIG. 35 is a schematic view of an exemplary flexible piezoelectric sensor.
Figure 36:
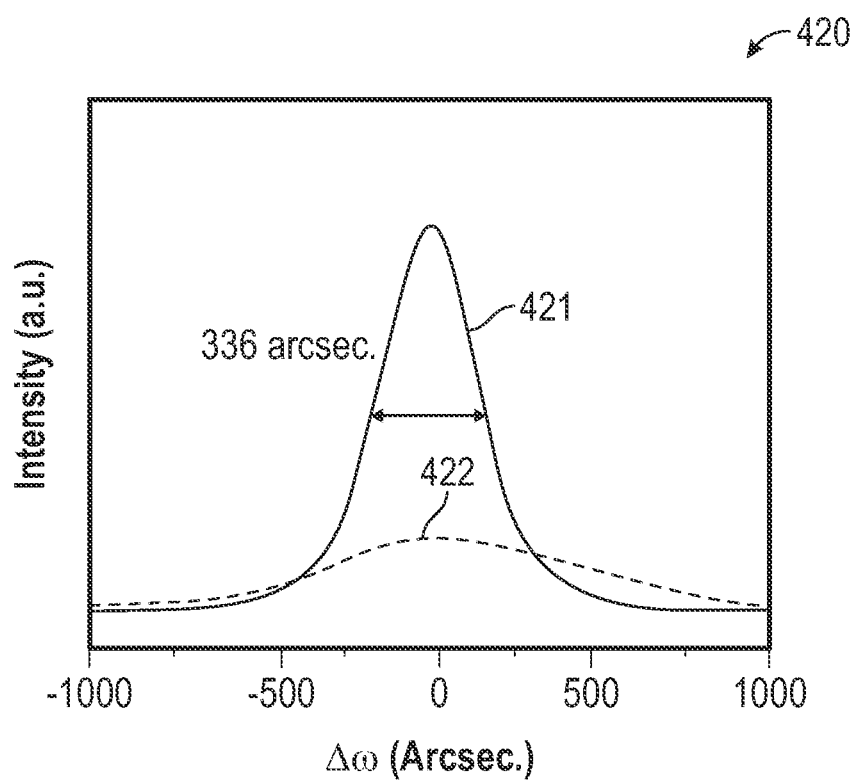
FIG. 36 is a graph illustrating X-ray diffraction characterization of a single-crystalline III-Nitride thin film along the GaN (0002) plane.
Figure 37:
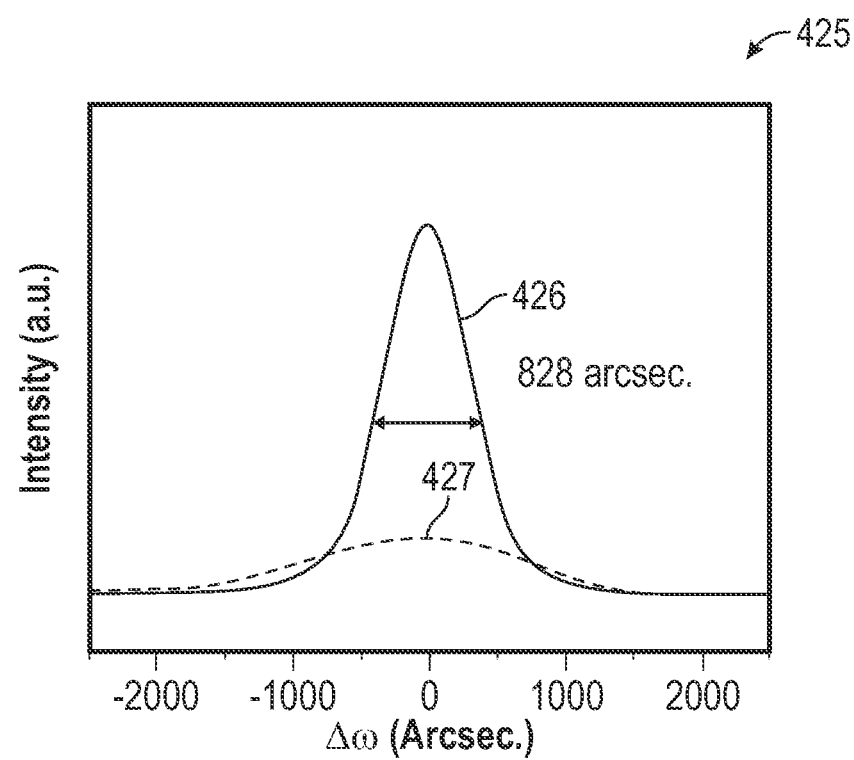
FIG. 37 is a graph illustrating X-ray diffraction characterization of a single-crystalline III-Nitride thin film along the GaN (10-12) plane.

Referring now to FIGS. 35-37, a fabricated F-PEMS 410 produced as part of this study is shown in FIG. 35. F-PEMS 410 having a flexible single-crystalline III-N film 412 sandwiched between the electrodes 414 and 416 encapsulated in PDMS 418. The F-PEMS 410 is conformal for the attachment of any skin surface and small enough for minimally invasive sensing. Furthermore, the output signal of the sensor-PEMS 410 was higher than that of a rigid sensor with uniform deformation. F-PEMS 410 was tested under flat and bending test conditions using a scanning-electron microscopy (SEM). The F-PEMS 410 surfaces were crack-free without surface features regardless of bending conditions, confirming that no bulk defect was generated even with a significant degree of bending.

Characteristics of Piezoelectric Sensing Element

The crystalline orientation and quality of the piezoelectric sensing element were investigated by high-resolution X-ray diffraction (HR-XRD). The III-N film on the Si substrate was epitaxially grown to produce the single-crystalline wurtzite structure with a surface of (0001) plane. A III-N film's out-of-plane growth direction is aligned in a [0001] direction of wurtzite structure, which is confirmed by the strong presence of (0001) peaks, such as (0002) and (0004). Therefore, a d33 piezoelectric structure was constructed, since the sensing element is sandwiched between two electrodes. Very sharp (0002) peaks of the III-N layers for both rigid and flexible substrates indicated the high crystalline quality of the sensing element before and after the fabrication of the device. Moreover, no other peak of wurtzite GaN, $Al_xGa_{1-x}N$, and AlN was observed in the 2θ-ω scan of XRD. Six sharp peaks were located at every 60° in the rotational scans (ϕ scan) around GaN {1012}planes, i.e., six-fold rotational symmetry of the hexagonal-lattice structure (wurtzite), indicating that all the grains perfectly aligned in both in-plane and out-of-plane directions. Such XRD results confirm the single-crystallinity of the III-N film. After the transfer process of the III-N film, the peaks were maintained, which indicated no structural changes.

Referring to FIGS. 36 and 37, graphs 420 and 425 are shown. Particularly, graph 420 illustrates rocking curves for a single-crystalline III-N thin film on a rigid (Si) substrate (curve 421) and a flexible (Cu/PDMS) substrate (curve 422) for the GaN (0002) plane. Graph 425 similarly illustrates rocking curves 421 and 422 for the III-N thin film on the rigid substrate (curve 426) and flexible substrate (curve 427) for the (1012) plane. For the single-crystalline thin films, the density of crystalline line defects were estimated from the rocking curves (w scans) of symmetric and asymmetric planes, as shown in graphs 420 and 425 of FIGS. 36 and 37, respectively. The full-width at half-maximum values of the GaN (0002) and GaN (1012) peaks on Si (curves 421 and 426 of graphs 420 and 425, respectively) were 336 arc-seconds (arc-sec.) and 828 arc-sec., respectively. The density of threading dislocations of the single-crystalline GaN film was calculated to be approximately $3.2 \times 10^9$ cm$^{-2}$. Such a low density of line defects in single-crystalline material where no grain boundary exists is important to reduce the leakage between the electrodes and to enhance the sensitivity of the sensor. The peaks in the rocking curves of the flexible substrate (curves 422 and 427 of graphs 420 and 425, respectively) were broader than those of the Si substrate. This phenomenon was attributed to the wavy or curved nature of the sample rather than the degradation of crystalline quality itself. The intensities of GaN peaks on a flexible substrate, i.e., after the fabrication were lower than those on Si substrate, possibly due to the buried location of GaN under a top electrode.

Sensing Mechanism of Eye Movements

Figure 38:
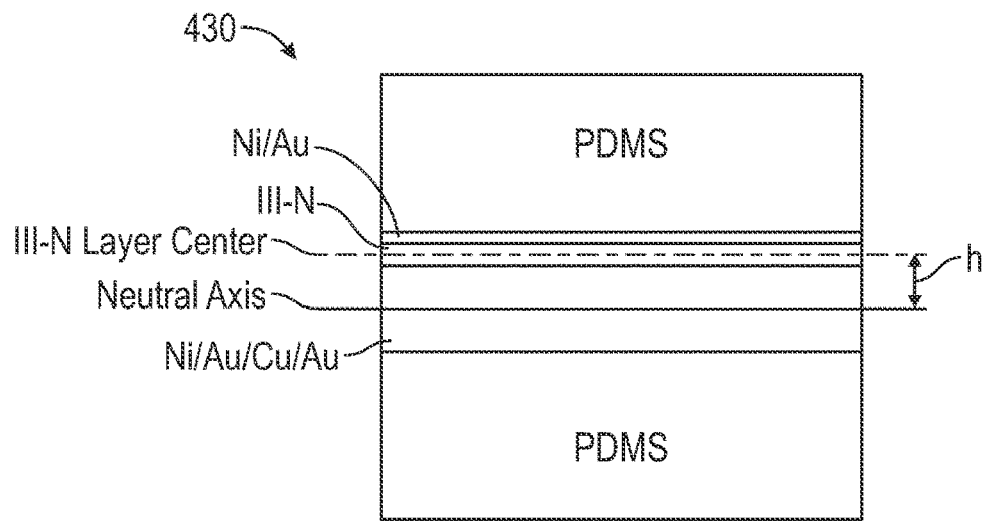
FIG. 38 is a side cross-sectional view of an exemplary flexible piezoelectric sensor.
Figure 39:
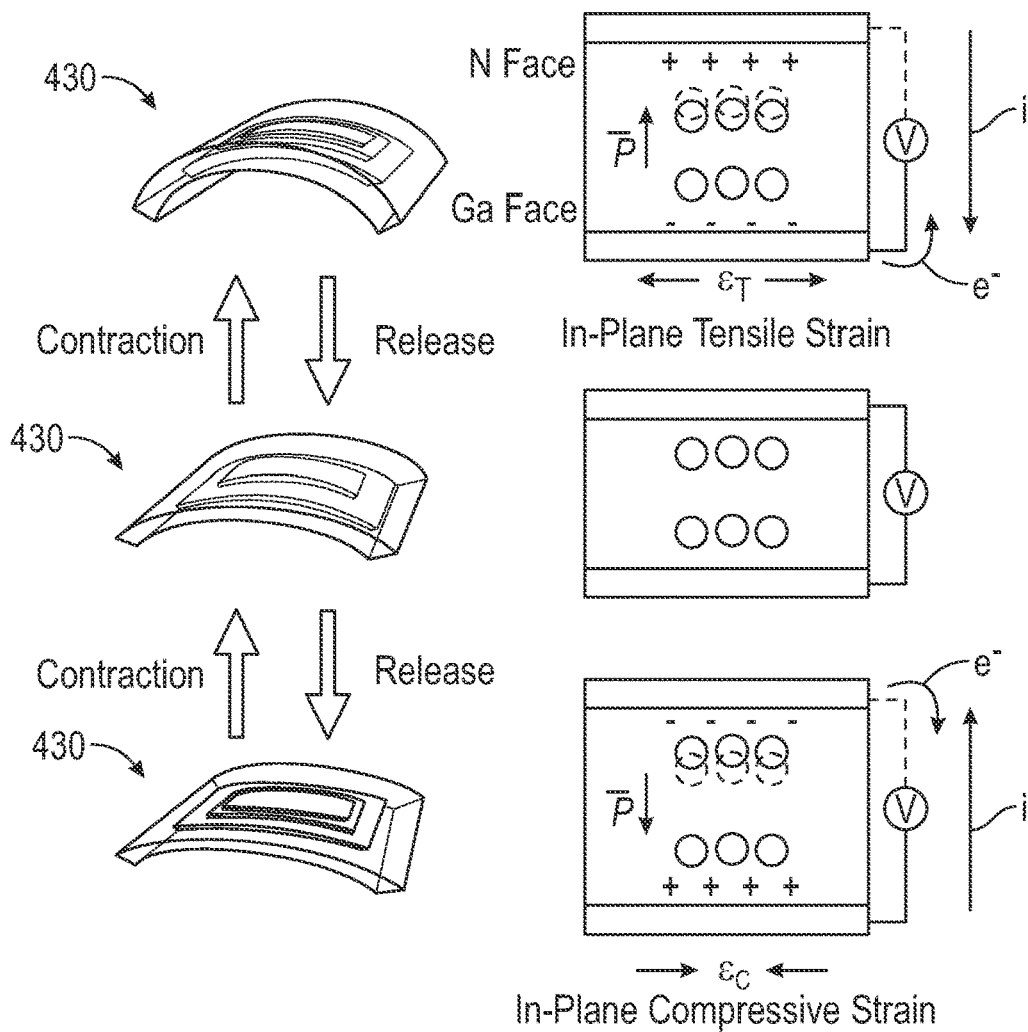
FIG. 39 is a schematic of a flexible piezoelectric sensor in different states.

Referring to FIGS. 38 and 39, as part of this study, a piezoelectric sensor 430 (i.e., a F-PEMS) was attached on a curved part of the skin near the eyes of a test subject. After the attachment, the sensor 430 was initially slightly bent depending on the contour of the skin of a face (shown at the middle of FIG. 39). When the bending degree of the sensor 430 was changed by the movement of the skin or muscles underneath, the change in piezoelectric polarization of the III-N film of the sensor 430 occurred. Because the bottom electrode of sensor 430 was significantly thicker than the III-N film, a neutral plane (shown in FIG. 38) of the sensor 430 was located in the Cu layer of the electrode (shown in FIG. 38). This configuration induced only one type of piezoelectric polarization change (positive or negative) depending on the bending mode.

Figure 40:
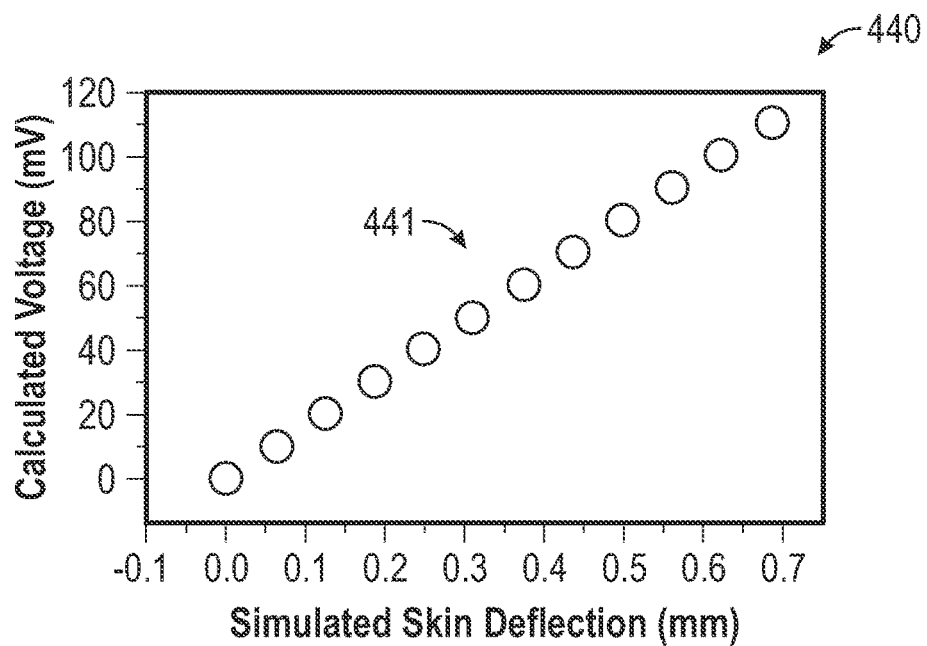
FIG. 40 is a graph illustrating a calculated output voltage from a flexible piezoelectric sensor as a function of simulated skin deflection.

When the sensor was further bent (shown in FIG. 39), in-plane tensile strain was applied and an upward piezoelectric polarization was accordingly induced. As a result, positive and negative charges were induced on the top (N-face) and bottom (Ga-face) surfaces, respectively. The electrical current flowed from top to bottom electrodes through the external wires because of the free electron movement to cancel out the piezoelectric charges on the surfaces of GaN (shown at the top of FIG. 39). Thus, the positive voltage output was measured. When the sensor was flattened, an in-plane compressive strain was applied and the negative voltage was measured (shown at the bottom of FIG. 39). Further bending and flattening resulted in opposite signs in the output voltage of the sensor 430. The change in skin contour by the eye movement is subtle; therefore, the piezoelectric sensor should be very sensitive to generate a substantial magnitude of the signal output voltage. Mathematical modeling software (COMSOL Multiphysics® and MATLAB®) was used to theoretically predict the output. Several parameters were applied including elastic modulus, Poisson ratio, unit weight, the thickness of film, sensor dimension (x and y), and applied load. Referring to FIG. 40, a graph 440 is shown illustrating the numerically simulated deflection and corresponding output voltages 441 of the piezoelectric sensor 430, confirming that the sensor 430 was sensitive enough to measure the subtle contour change.

Figure 41:
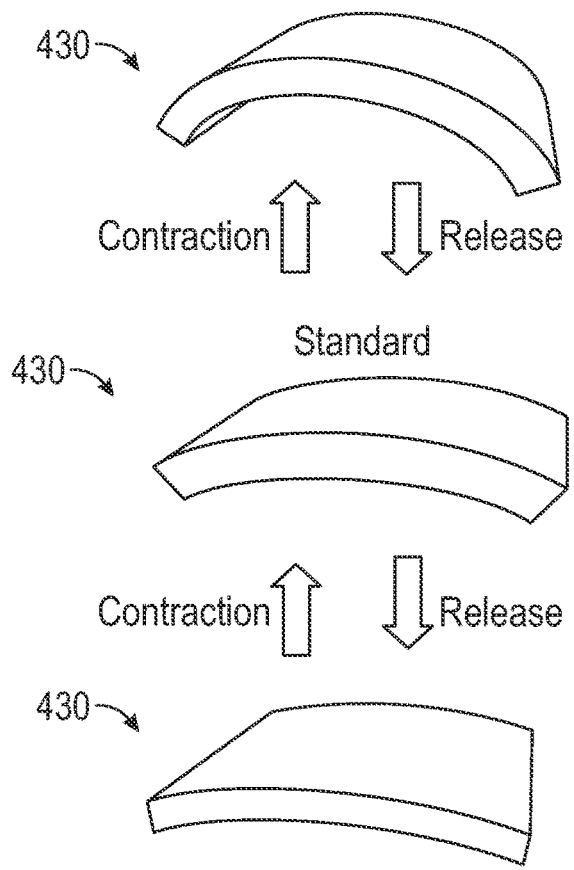
FIG. 41 is a perspective view of an embodiment of a piezoelectric sensor.

As described above, accurate and reliable sensing of eye movement in a noninvasive and comfortable way is important, therefore, the sensing on a temple area over upper and lower eyelid areas was preferred during the study. While the strain change on the skin of upper and lower eyelids is relatively straightforward, the skin contour change of the temple area is associated with muscle movement. Referring to FIG. 41, the bending status of the piezoelectric sensor 430 for contraction and release modes is shown.

The piezoelectric sensor 430 can be further bent or flattened from the initial condition by the eye blinking or eyeball motion by contraction and release force from muscle movement. Therefore, the modes of eye movements generate different output voltages, i.e., opposite signs and varied magnitude. For the eye blinking, the main protractor of the eyelid, which serves to close the eye, is the orbicularis oculi and it is connected to the temple via ligament. The ligament underneath of the temple is tightened or loosened for opening or closing of the eyelid during the eye-blinking process, respectively. For the eyeball movements, different muscles are involved. Among these muscles, lateral rectus and medial rectus are principal parts for side-glance of the eyeball, which can be displayed with simulated results. The muscles and ligament underneath the temple area are contracted when the eyeball moves toward the temple side (right) and are expanded when the eyeball moves away from the temple side (left).

Eye-Blink Sensing

Figure 42:
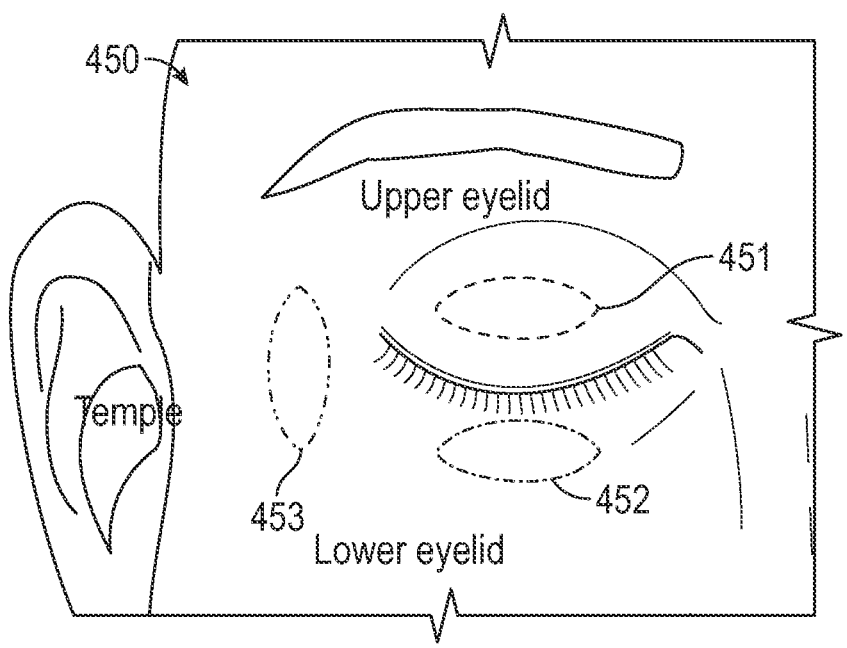
FIG. 42 is a schematic of different regions of a user's face.
Figure 43:
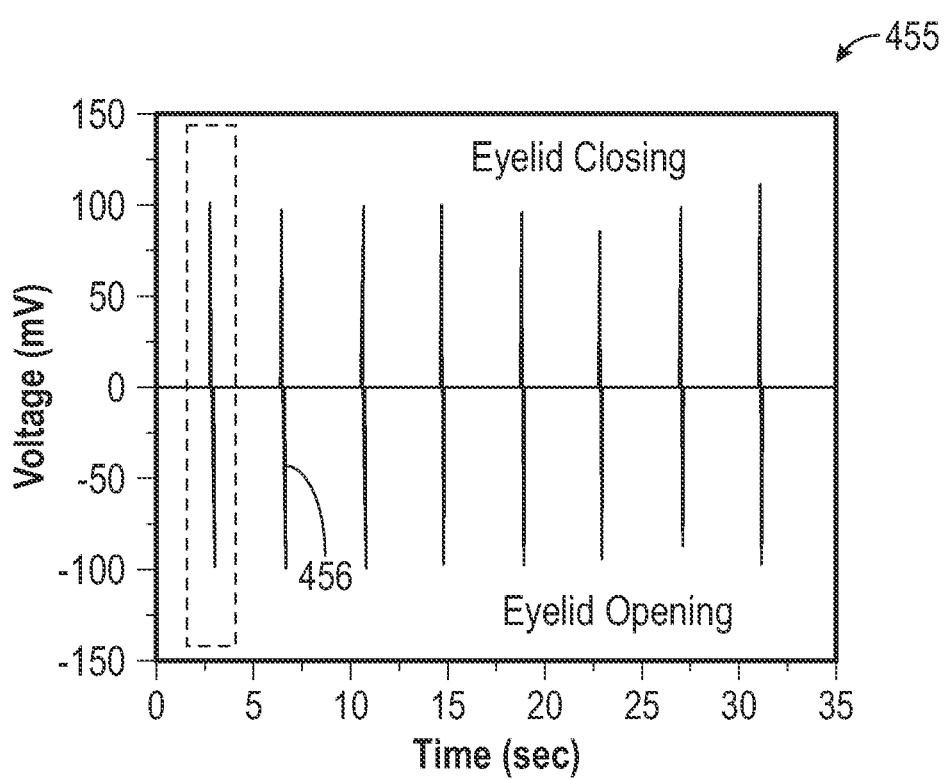
FIGS. 43-55 illustrate output voltages produced by exemplary flexible piezoelectric sensors positioned on a user's face.
Figure 44:
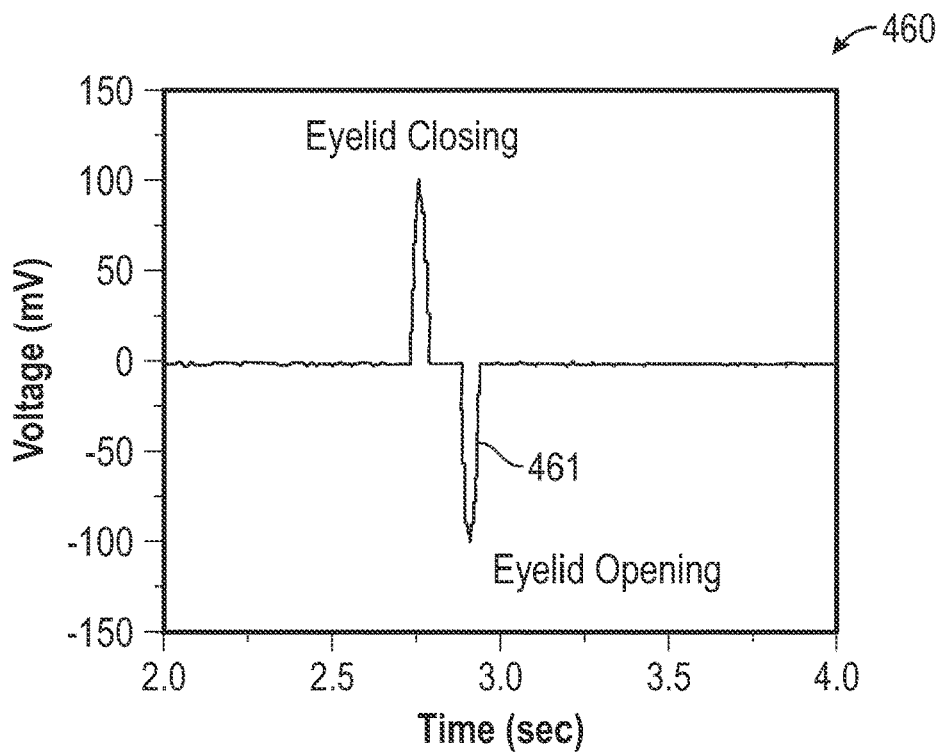

Referring to FIGS. 42-51, sensing characteristics for eye-blink movements are shown indicating that the F-PEMS (e.g., F-PEMS 410, piezoelectric sensor 430) yields substantial output voltage changes with various blink behaviors. Particularly, FIG. 42 shows three locations around the eye including images of a test subject 450 wearing the F-PEMS on the upper eyelid 451, lower eyelid 452, and temple 453 using a biocompatible tape. This adhesive material was strong enough to bond on human skin with high flexibility. It should be noted that the size of the F-PEMS (1×1 centimeters squared ($cm^2$)) was determined by the dicing size of the GaN/Si sample. The F-PEMS can be made significantly smaller without affecting the output voltage signal. The voltage output from sensors with different sizes including 0.25 $cm^2$ (0.5×0.5 $cm^2$) and 4 $cm^2$ (2×2 $cm^2$) was confirmed experimentally as being similar to those of the F-PEMS used in this study.

Figure 45:
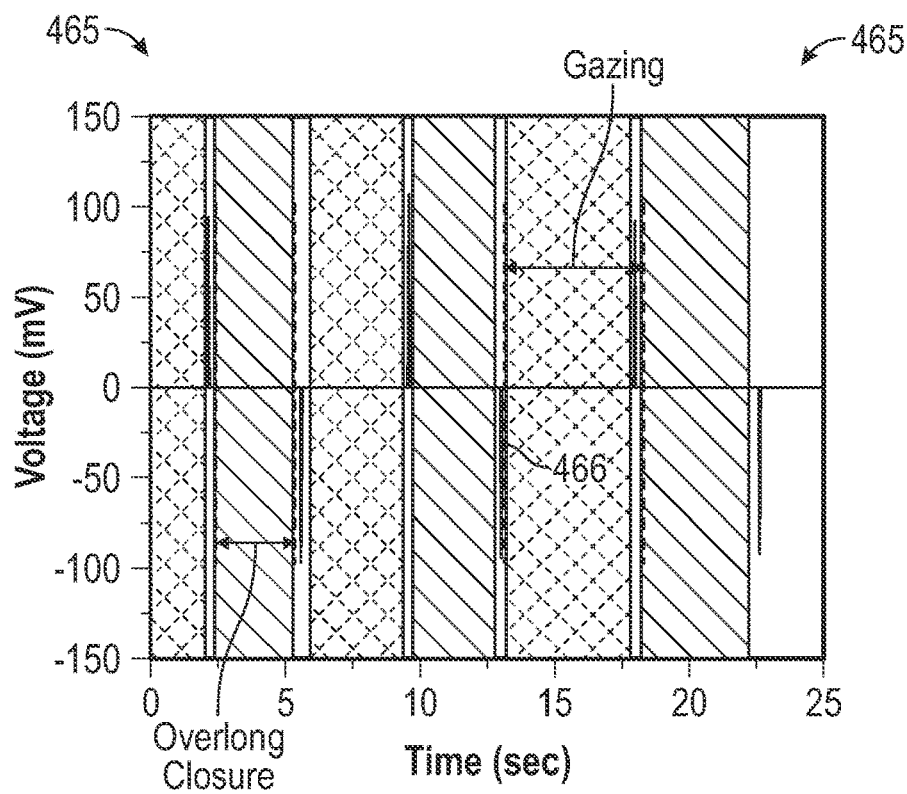
Figure 46:
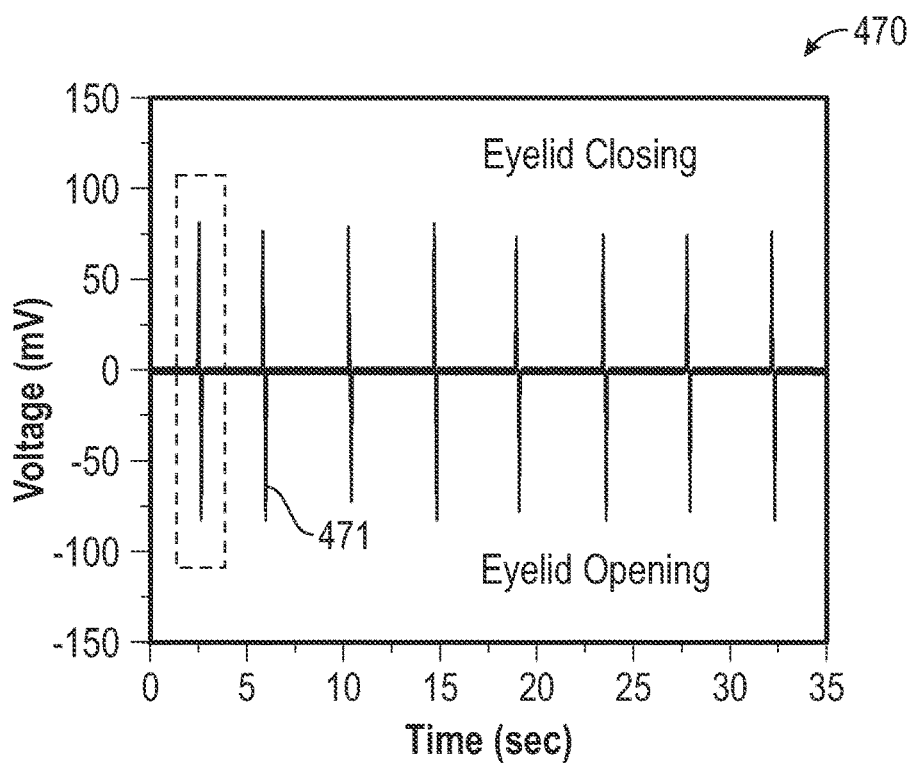
Figure 47:
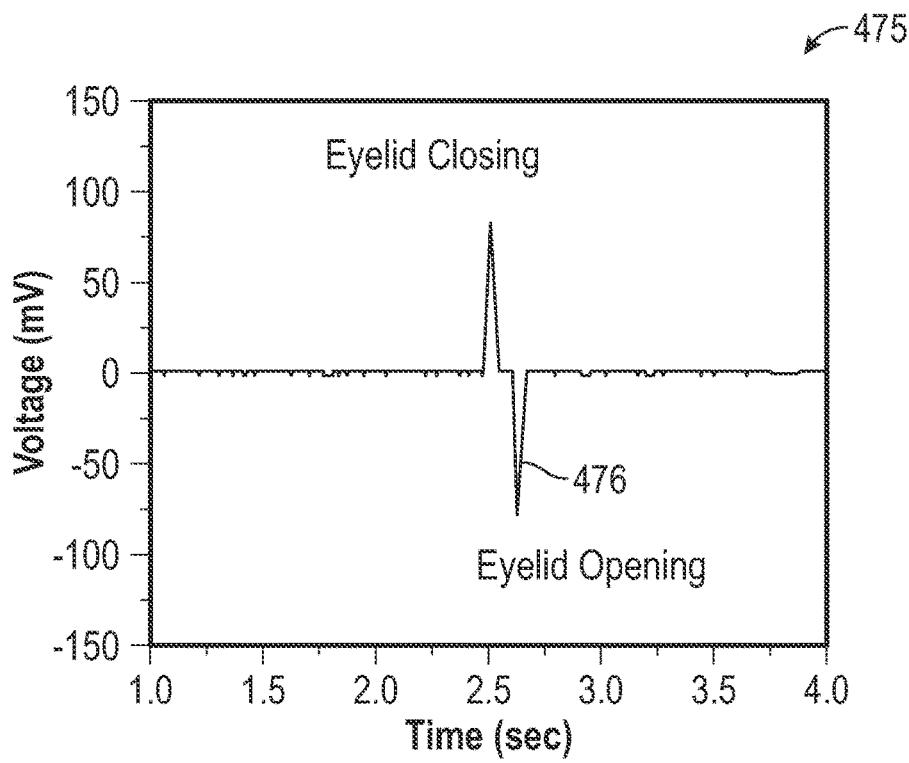
Figure 48:
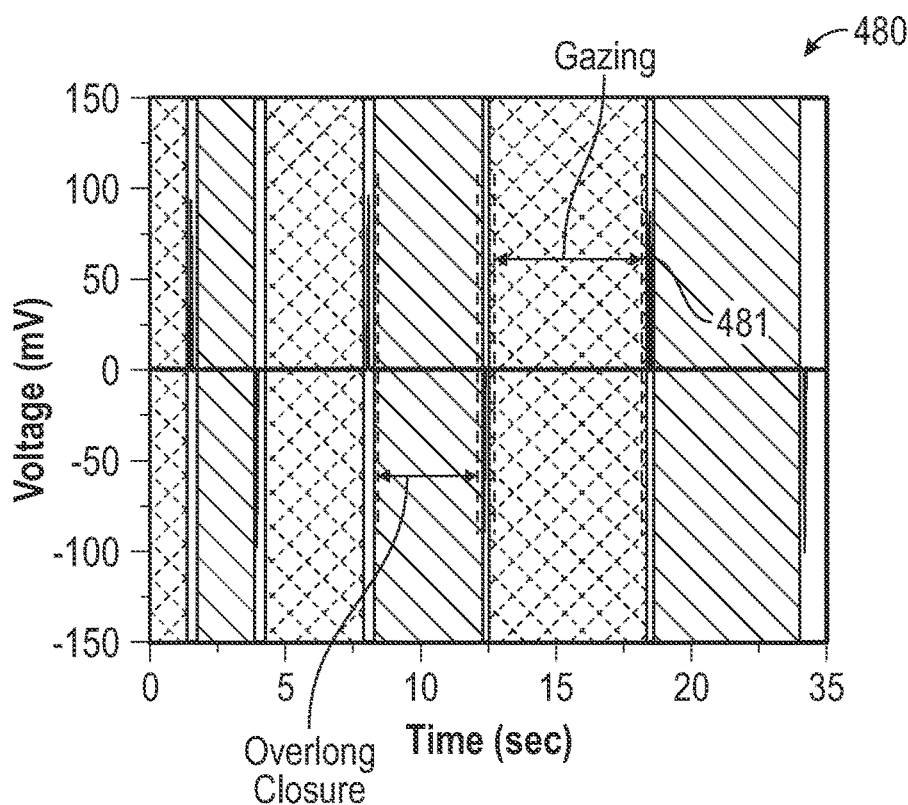
Figure 49:
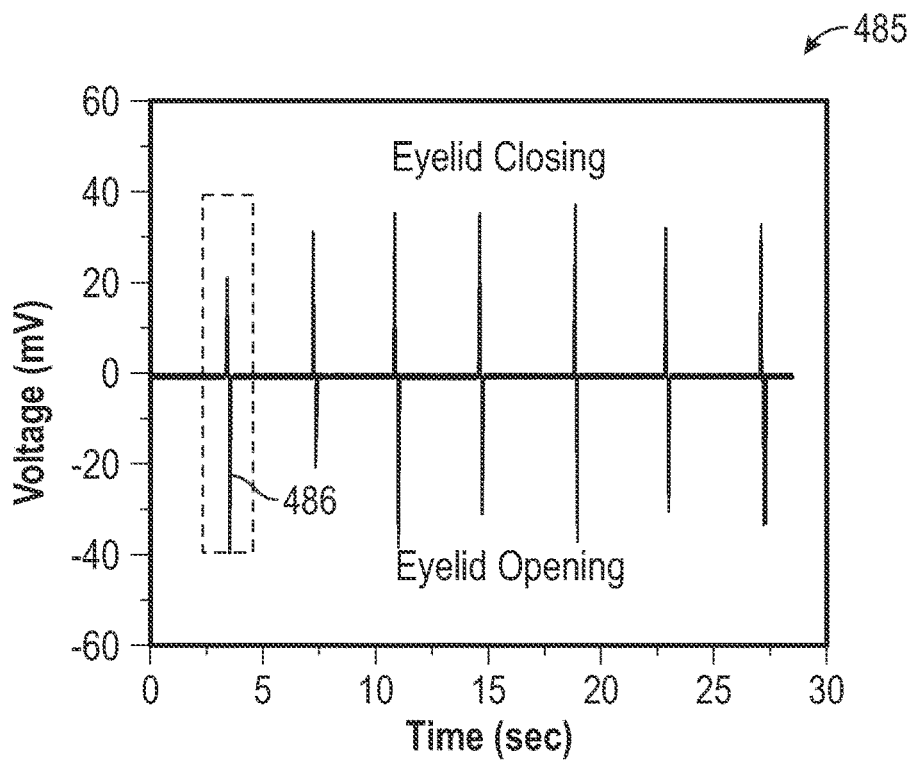
Figure 50:
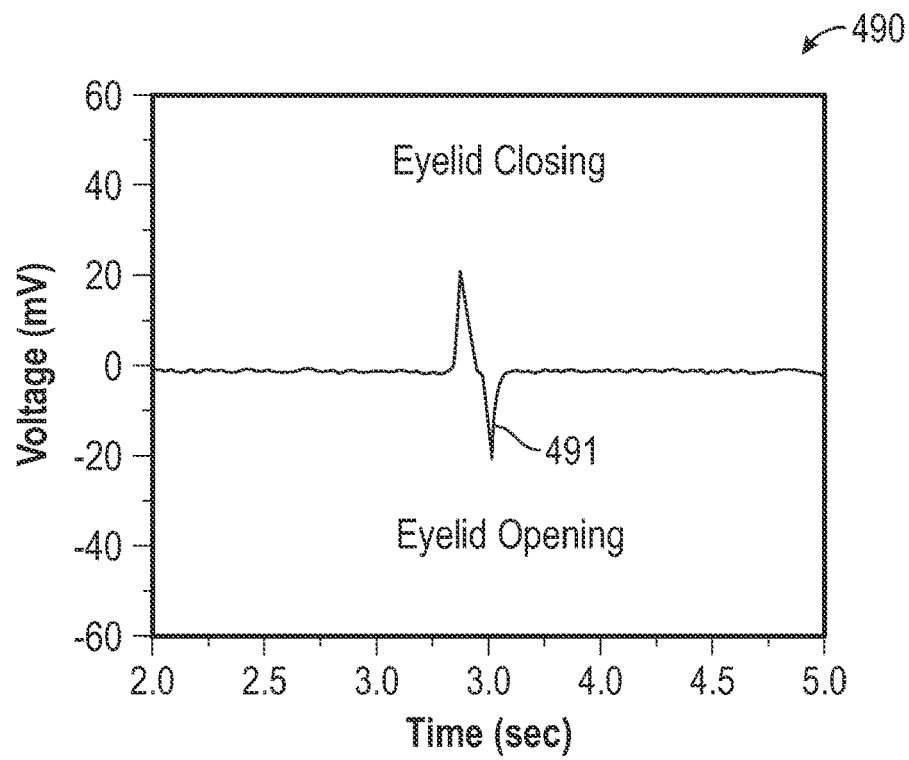
Figure 51:
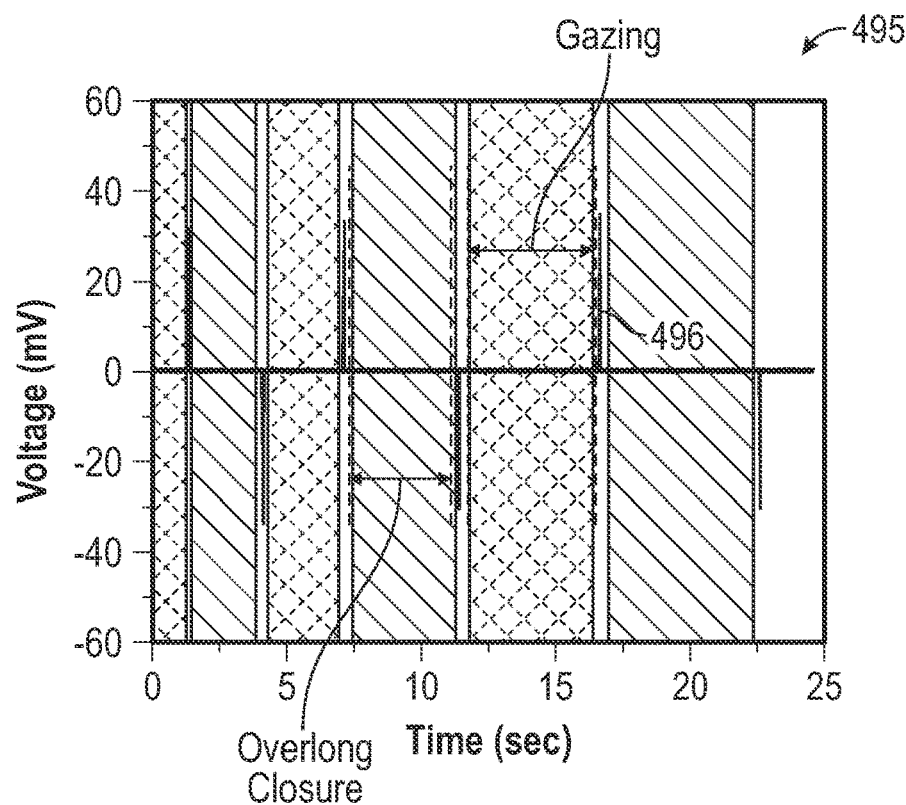

FIGS. 45-47 illustrate graphs 455, 460, and 465, respectively, of output voltages 456, 461, and 466 respectively, produced by the F-PEMS when positioned on the upper eyelid 451. FIGS. 46-48 illustrate graphs 470, 475, and 480, respectively, of output voltages 471, 476, and 4481 respectively, produced by the F-PEMS when positioned on the lower eyelid 452. FIGS. 49-51 illustrate graphs 485, 490, and 495, respectively, of output voltages 486, 491, and 496, respectively, produced by the F-PEMS when positioned on the temple 453. Additionally, graphs 455, 470, and 485 illustrate overall sensing characteristics; graphs 460, 475, and 490 illustrate a single eyelid opening/eyelid closing event; and graphs 465, 480, and 495 illustrate eyelid motion including overlong closure and overlong gazing instead of eye blinking.

The overall average values of the output voltages were 97.85 millivolts (mV) and −96.02 mV (illustrated by graphs 455 and 460) for closing and opening when the F-PEMS was positioned on the upper eyelid 451; 78.31 mV and −79.42 mV for closing and opening when the F-PEMS was positioned on the lower eyelid 452 (illustrated by graphs 470 and 475); and 32.3 mV and −30.3 mV for closing and opening when the F-PEMS was positioned on the temple 453 (illustrated by graphs 485 and 490). The absolute values in the change were highest for the upper eyelid 451 and lowest for the temple 453, which is related to the difference in the crooked level of the face parts. It is not surprising that the previous studies only show measurements from the eyelid area, which causes discomfort while wearing for the measurements. It this study, Measurement from the temple 453 was demonstrated in this study. Signal-to-noise ratios (SNR, S/R) were 49.26 decibels (dB), 47.88 dB, and 40.13 dB for the measurements on the upper eyelid 451, lower eyelid 452, and temple 453, respectively. Not intending to be bound by any particular theory, the SNR was determined in accordance with the following Equation where $V_{signal}$ represents the average value of output voltages and $V_{noise}$ represents the averaged background signals:

$$SNR_{dB} = 20\log\left(\frac{V_{signal}}{V_{noise}}\right) \quad (1)$$

All the SNR values were greater than 40 dB, suggesting that the voltage values from the F-PEMS on the temple 453 were sufficient to communicate in wireless data.

Graphs 460, 475, and 490 generated the positive and negative voltage outputs for the eyelid closing and opening, respectively, enabling to distinguish four stages of a normal eye blink motion, i.e., closing, closure, opening, and gazing. The eye closing corresponds to the output positively rising from zero to the peak. The output drops to and remains at zero until the further movement of the eyelid, corresponding to eye closure. The changes in voltage output 461, 476, and 491 were in the opposite direction with increasing magnitude during the eye-opening, i.e., moving from zero to the valley. The voltage outputs 461, 476, and 491 changed to and remained at zero during the gazing stage. The rapid eye blinking was also measured with higher frequency (0.24 Hertz (Hz)→1.67 Hz). The flickering rate was influenced by short-term changes in the brain, such as tiredness and/or sleepiness. The voltage values were very similar to the outputs of blinking at a normal rate. These results indicated that the F-PEMS can be utilized to detect various eyelid movements for the evaluation of normal blinking, dry eyes, and drowsiness.

Long-term stability is one of the key parameters for the operation of sensors. The F-PEMS was tested on the skin of a human test subject by continuous monitoring of eye blinking of the subject for 10 minutes (min) followed by regular measurement every 30 min for approximately 10 hours (h). During the test, the subject wore the sensor during their daily routine without discomfort thanks to the conformal, compact, and noninvasive nature of the F-PEMS. No degradation of the voltage output was observed for both the continuous monitoring and long-term monitoring. No performance issue was expected for long-term continuous monitoring. The F-PEMS can be reused by the subject in the following days. The stability and durability of the F-PEMS were thus confirmed.

Fatigue and Drowsiness Detection

The degree of fatigue and drowsiness of a subject can be estimated by blink frequency, blink duration (delays of eye reopening), and PERCLOS (percentage of eye closure). A lid closure that lasts more than about 500 milliseconds (ms) and covers the pupil for that time is usually defined as a microsleep. To simulate the state of the microsleep, overlong closure was investigated using the same positions. The overlong closure is of great interest in assessing workers, warfighters, and driving safety to detect blind working, blind walking, and drowsy driving, respectively. Graphs 465, 480, and 495 illustrate that the F-PEMS was capable of detecting microsleep in the test subject in real-time. As shown in graphs 465, 480, and 495, sections of overlong closure and gazing are distinguished by the voltages upon the initiation of eyelid movement. For example, the gap between the positive and negative potentials was "overlong closure," whereas the interval between the negative and positive outputs was "gazing." Unlike the computer-vision-based ETS, the detection does not require additional calibration. The F-PEMS can directly provide the duration time for the overlong closure from the output change. Also, the response time of the F-PEMS was brief enough to distinguish the four stages of eye blinking.

Tiredness in an individual can be recognized through changes in the individual's eyes, especially the blinking of eyes. Also, when people are exhausted, their eyes typically close unconsciously while walking and driving. To investigate the fatigued eye, we simulated the status of dozing off was simulated whereby the test subject closed their eyes halfway (here, almost half and 75% closed) and blinked their eyes alternating between normal blinks and half-blinks.

Figure 52:
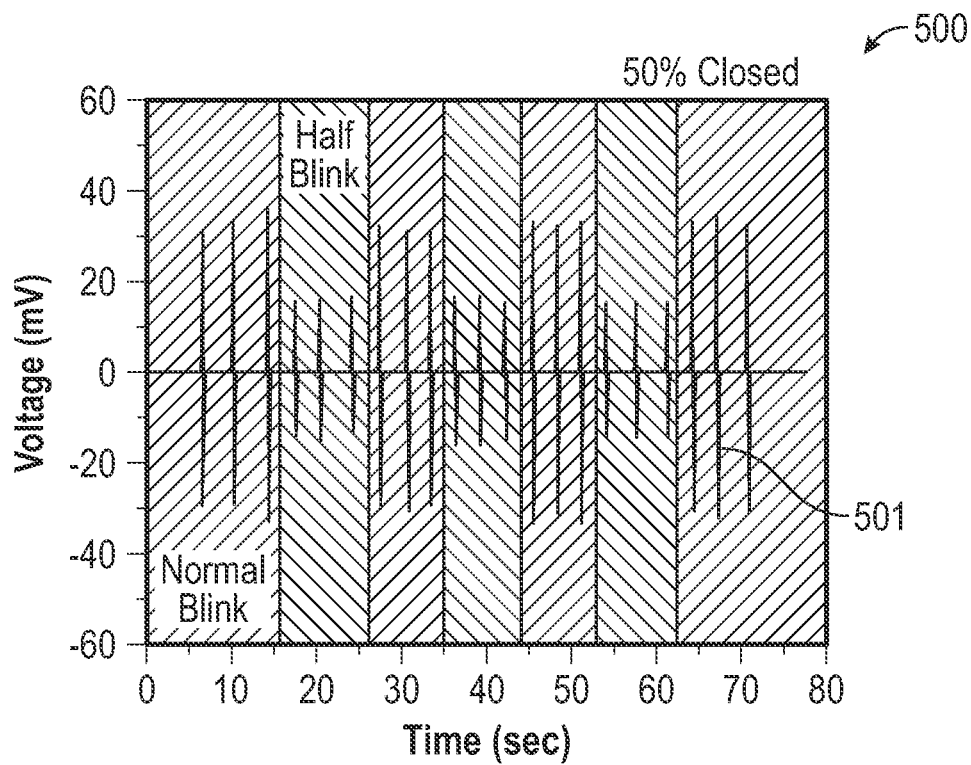
Figure 53:
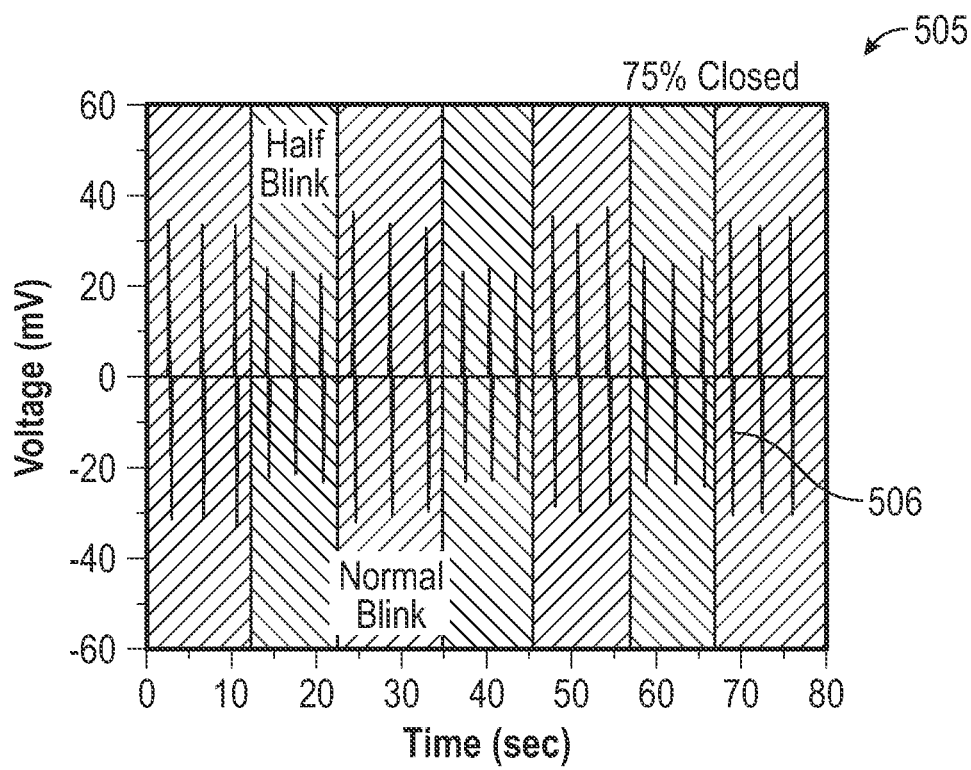

Referring to FIGS. 52 and 53, graphs 500 and 505 are shown illustrating voltage outputs 501 and 506, respectively, generated by the F-PEMS when positioned on the test subject's eye with the subject half-blinking in order to mimic a fatigued eye. Additionally, graph 500 illustrates the response of the F-PEMS when the subject closes 50% of their eye when half-blinking while graph 505 illustrates the response of the F-PEMS when the subject closes 75% of their eye when half-blinking. The voltage outputs 501 and 506 were relatively small value approximately 50% for output 501 and 72% for output 506), which means that we could discern the condition of the eye from voltage outputs 501 and 506. The results from other parts (upper eyelid and lower eyelid) with the half-closed condition showed a similar tendency to the voltage outputs from the temple area.

Eyeball-Movement Sensing

Figure 54:
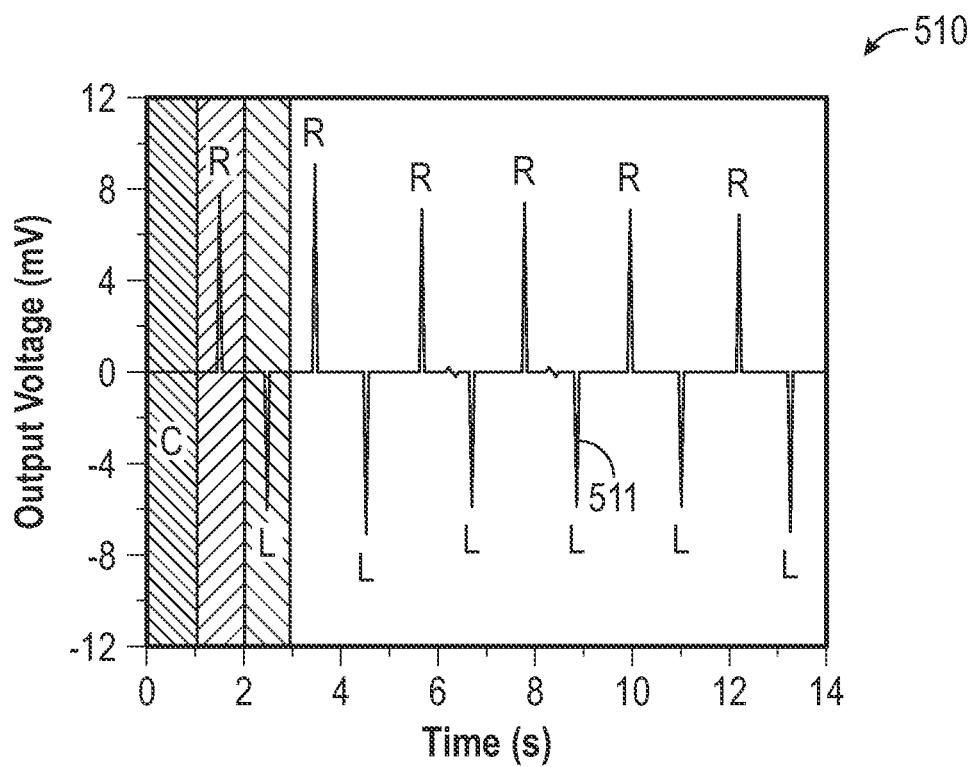
Figure 55:
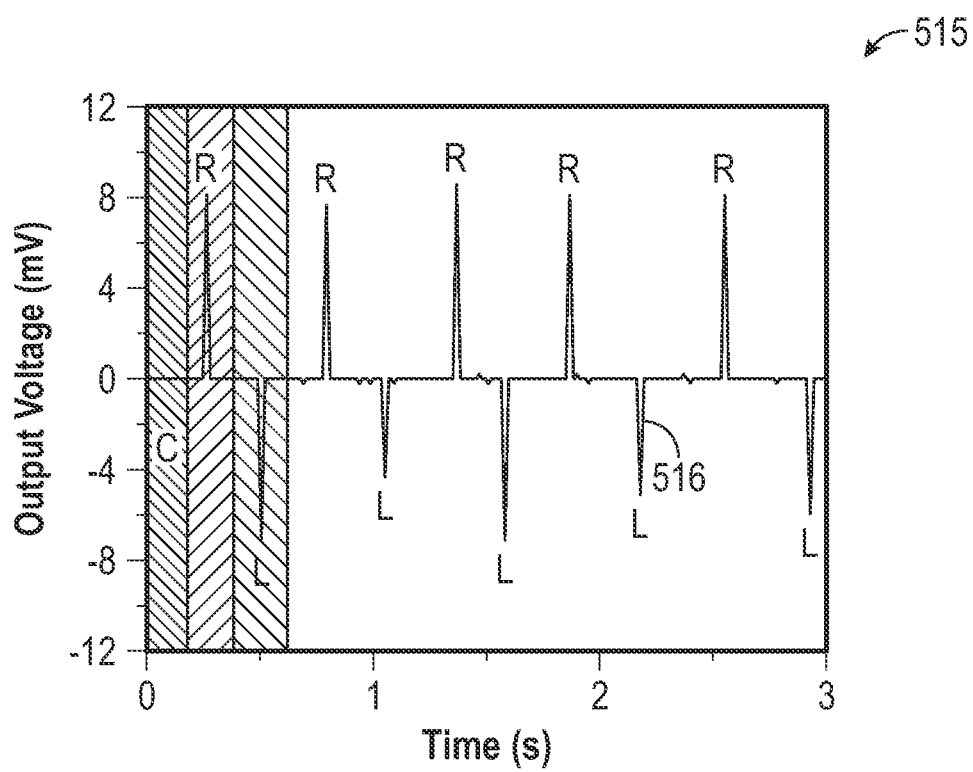

In addition to the sensing of eye blink for the detection of eye fatigue and drowsiness, the F-PEMS can measure the movement of the eyeball, which is related to sleeping patterns, the additional diagnosis of brain-related diseases, and eye tracking in AR/VR systems. Referring to FIGS. 54 and 55, graphs 510 and 515 are shown illustrating voltage outputs 511 and 516, respectively, generated by the F-PEMS when positioned on the test subject's eye with the subject looking repeatedly from a center (C) position, a right (R) position, and a left (L) position. Additionally, graph 510 illustrates the response of the F-PEMS when the subject moves their eye slowly while graph 515 illustrates the response of the F-PEMS when the subject moves their eye rapidly.

When the eyeball moved to the right, i.e., moving toward the sensor side, positive values were measured. In contrast, when the eyeball moved in the opposite direction, i.e., moving away from the sensor side, negative values were obtained. This output is different from the signal of the EOG that measures the potential difference between cornea and retina, which is influenced by numerous external conditions, e.g., light intensity, number of electrodes, skin status, and noise from contact resistance. As the contraction of the lateral rectus pulled the test subject's eye away from the nose (right seeing), the sensor was further bent. Conversely, as the contraction of the medial rectus pulled the test subject's eye toward the nose (left seeing), the sensor was flattened. The eyeball moving to the right and the left sides corresponded to contraction and release of the F-PEMS, respectively.

Additionally, when the eyeball moved toward the sensor side, further bending of the sensor occurred, hence positive voltage outputs (voltage outputs 511 and 516) were generated. When the eyeball moved away from the sensor side, the negative voltage output was generated. The output characteristics were measured in both cases of slow (voltage output 511) (≈0.5 Hz) and rapid (voltage output 516) (≈1.9 Hz) eye movement, showing similar output voltage values regardless of the speed of the motion. In graph 515, the initiation of the lateral eye movement can be detected with a fast response time. The output from different sensor positions (upper eyelid and lower eyelid) showed a similar trend only with higher output voltage values, attributed to relatively larger deformation of the F-PEMS. The overall values of voltage output were different for eyelid movements (≈30 mV) and eyeball movements (≈10 mV). Therefore, each movement was distinguishable for the sensing of combined movements of eye blinking and eyeball moving. Moreover, further detailed movement of eyeballs (vertical and oblique directions and rotational movements) and eyelid (left and right separately) could be detected if arrayed (e.g., 1×3) sensors were attached on both sides of the temples.

CONCLUSIONS OF THE STUDY

A flexible piezoelectric sensor or F-PEMS was designed, fabricated, and tested to develop a personal safety, behavior, and healthcare monitoring sensing network. A stable and safe piezoelectric single-crystalline III-N thin film was epitaxially grown on a Si (111) substrate and then transferred to a flexible PDMS substrate followed by the electrode formation. The fabricated F-PEMS was tested on several different parts around the eyes, including the upper eyelid, lower eyelid, and temple area. The F-PEMS was estimated to generate substantial output voltage signals enough to detect small deflections of muscles and skins caused by eyelid and eyeball movements based on numerical simulation and demonstrated to measure normal eye blinking with signal-to-noise ratios of higher than 40 dB, confirming high sensitivity and usability for wireless communication systems. The F-PEMS was especially capable to detect various movements of eyelid and eyeballs from the most-comfortably-wearable temple area. This noninvasive, nontoxic, and easily-wearable F-PEMS was demonstrated to detect eye blink frequency, blink duration, and percent of eye closure to function as an objective indicator of eye strain, fatigue, and drowsiness. The F-PEMS was also demonstrated to measure lateral movements of eyeballs, which are distinguished from the eye blink, for the potential use of medical diagnosis indicators of autism, ADHD, stroke, Alzheimer and Parkinson's disease as well as in industrial applications such as VR and AR in remote control of robots.

While embodiments of the disclosure have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the disclosure. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A system for tracking an eye of a user, the system comprising:
   one or more piezoelectric sensors positionable on the face of the user and into contact with the user's skin; and
   an eye tracking computer system in signal communication with the one or more piezoelectric sensors so as to receive signals from the one or more piezoelectric sensors;
   wherein the computer system is configured to detect movement in at least one direction of the eye of the user based on the signals received by the computer system from the one or more piezoelectric sensors in response to flexure of the one or more piezoelectric sensors when positioned on the face of the user in one or more locations each spaced from the eyelids of the user.

2. The eye tracking system of claim 1, wherein the computer system is configured to detect the movement in the at least one direction of the eye of the user when the one or more piezoelectric sensors are positioned on the temple of the user.

3. The eye tracking system of claim 1, wherein:
   the one or more piezoelectric sensors comprises a plurality of the piezoelectric sensors positionable on the face of the user; and
   the computer system is configured to detect movement of the eye of the user in both a lateral direction and a vertical direction orthogonal to the lateral direction when the plurality of the piezoelectric sensors are positioned on the face of the user in a plurality of locations each spaced from the eyelids of the user.

4. The eye tracking system of claim 3, wherein the computer system is configured to compare the signals produced by the plurality of the piezoelectric sensors to detect the movement of the eye of the user in both the lateral direction and the vertical direction when the plurality of the piezoelectric sensors are positioned on the face of the user in the plurality of locations each spaced from the eyelids of the user.

5. The eye tracking system of claim 3, wherein the computer system is configured to detect movement of the eye of the user in a diagonal direction that is at a non-zero angle to both the lateral direction and the vertical direction when the plurality of the piezoelectric sensors are positioned on the face of the user in the plurality of locations each spaced from the eyelids of the user.

6. The eye tracking system of claim 1, wherein the computer system is configured to detect movement of the eye of the user in a rotational direction when the plurality of the piezoelectric sensors are positioned on the face of the user in the plurality of locations each spaced from the eyelids of the user.

7. The eye tracking system of claim 1, wherein the signals produced by the one or more piezoelectric sensors are contingent upon the deflection of the facial skin of the user upon which the one or more piezoelectric sensors are positioned.

8. The eye tracking system of claim 1, wherein each of the one or more piezoelectric sensors comprises a pair of electrodes and a piezoelectric film positioned between the pair of electrodes.

9. The eye tracking system of claim 8, wherein the piezoelectric film comprises at least one of aluminum nitride, gallium nitride, and indium nitride.

10. The eye tracking system of claim 8, wherein each of the one or more piezoelectric sensors comprises an outer insulating layer sealing the piezoelectric film and the pair of electrodes from the external environment.

11. The eye tracking system of claim 8, wherein each of the one or more piezoelectric sensors comprises an adhesive pad for removably attaching the one or more piezoelectric sensors to the face of the user.

12. The eye tracking system of claim 1, wherein:
   the computer system is configured to generate an image based on the detection of the movement of the eye of the user in the at least one direction; and the computer system comprises a visual display configured to indicate the image to the user.

13. A method for tracking an eye of a user, the method comprising:
- (a) producing signals from one or more piezoelectric sensors in response to the user moving their eye in at least one direction, wherein the one or more piezoelectric sensors are positioned on the face of the user and in contact with the user's skin in one or more locations each spaced from the eyelids of the user in response to the user;
- (b) receiving by a computer system the signals produced by the one or more piezoelectric sensors; and
- (c) detecting by the computer system movement in the at least one direction of the eye of the user based on the signals received from the one or more piezoelectric sensors in response to flexure of the one or more piezoelectric sensors positions on the face of the user.

14. The method of claim 13, wherein:
- (a) comprises producing signals from a plurality of the piezoelectric sensors in response to the user moving their eye in at least one direction, wherein the one or more piezoelectric sensors are positioned on the face of the user in one or more locations each spaced from the eyelids of the user in response to the user;
- (b) comprises receiving by the computer system the signals produced by the plurality of the piezoelectric sensors;
- (c) comprises detecting by the computer system movement of the eye of the user in both a lateral direction and a vertical direction orthogonal to the lateral direction; and optionally
- (c) comprises detecting by the computer system movement of the eye of the user in a diagonal direction that is at a non-zero angle to both the lateral direction and the vertical direction.

15. The method of claim 13, wherein:
- (a) comprises producing signals from a plurality of the piezoelectric sensors in response to the user moving their eye in at least one direction, wherein the one or more piezoelectric sensors are positioned on the face of the user in one or more locations each spaced from the eyelids of the user in response to the user;
- (b) comprises receiving by the computer system the signals produced by the plurality of the piezoelectric sensors; and
- (c) comprises detecting by the computer system movement of the eye of the user in a rotational direction.

* * * * *